United States Patent
Ragg

(10) Patent No.: US 11,529,451 B2
(45) Date of Patent: Dec. 20, 2022

(54) METHOD AND DEVICE FOR TREATING VENOUS INSUFFICIENCY AND VARICOSE VEINS

(71) Applicant: ANGIOCLINIC AG, Lachen (CH)

(72) Inventor: Johann Christof Ragg, Berlin (DE)

(73) Assignee: ANGIOCLINIC AG, Lachen (CH)

( * ) Notice: Subject to any disclaimer, the term of this patent is extended or adjusted under 35 U.S.C. 154(b) by 728 days.

(21) Appl. No.: 14/396,690

(22) PCT Filed: Apr. 18, 2013

(86) PCT No.: PCT/EP2013/058066
§ 371 (c)(1),
(2) Date: Oct. 23, 2014

(87) PCT Pub. No.: WO2013/160180
PCT Pub. Date: Oct. 31, 2013

(65) Prior Publication Data
US 2015/0088051 A1    Mar. 26, 2015

(30) Foreign Application Priority Data

Apr. 24, 2012 (EP) .................................. 12165246

(51) Int. Cl.
| | | |
|---|---|---|
| A61M 1/00 | (2006.01) |
| A61B 17/00 | (2006.01) |
| A61M 25/00 | (2006.01) |
| A61M 25/01 | (2006.01) |
| A61B 17/12 | (2006.01) |
| A61K 9/12 | (2006.01) |
| A61K 31/08 | (2006.01) |
| A61K 47/02 | (2006.01) |
| A61K 47/32 | (2006.01) |

(52) U.S. Cl.
CPC ......... *A61M 1/85* (2021.05); *A61B 17/00491* (2013.01); *A61B 17/12131* (2013.01); *A61B 17/12186* (2013.01); *A61K 9/122* (2013.01); *A61K 31/08* (2013.01); *A61K 47/02* (2013.01); *A61K 47/32* (2013.01); *A61M 25/007* (2013.01); *A61M 25/01* (2013.01); *A61M 2025/0006* (2013.01); *A61M 2025/0175* (2013.01); *A61M 2202/02* (2013.01); *A61M 2210/12* (2013.01)

(58) Field of Classification Search
None
See application file for complete search history.

(56) References Cited

U.S. PATENT DOCUMENTS

| | | | |
|---|---|---|---|
| 5,735,813 A * | 4/1998 | Lewis ................ | A61M 25/065 604/164.01 |
| 2003/0120256 A1 | 6/2003 | Lary et al. | |
| 2005/0107738 A1 | 5/2005 | Slater et al. | |
| 2005/0245896 A1 | 11/2005 | Kucharczyk et al. | |
| 2007/0003489 A1 | 1/2007 | Wright et al. | |
| 2008/0245374 A1 * | 10/2008 | Agnew .............. | A61B 17/0057 128/887 |
| 2009/0069758 A1 * | 3/2009 | Bates ............... | A61B 17/00008 604/286 |
| 2010/0217306 A1 * | 8/2010 | Raabe .............. | A61B 17/00491 606/201 |

FOREIGN PATENT DOCUMENTS

| | | | | |
|---|---|---|---|---|
| EP | 1701701 A1 * | 9/2006 | ....... | A61B 17/00008 |
| WO | WO 2006/120461 | 11/2006 | | |
| WO | WO 2009/104189 | 6/2009 | | |
| WO | WO 2010/096717 | 8/2010 | | |
| WO | WO 2011/066278 | * | 6/2011 | |

OTHER PUBLICATIONS

International Search Report dated Jul. 1, 2014 in International Patent Application No. PCT/EP2013/058068.

* cited by examiner

*Primary Examiner* — David J Blanchard
*Assistant Examiner* — Sarah J Chickos
(74) *Attorney, Agent, or Firm* — Ballard Spahr LLP

(57) ABSTRACT

One larger [1] and one smaller tube [2], forming a functional unit with the smaller tube [2] positioned within the larger tube [1], both tubes are relocatable and demountable, both tubes with an aperture [3 and 4] at both ends, at least one aperture [5] being provided in the wall of the outer tube located at a distance of about between 1 mm and 10 cm from the tip [6], or several apertures positioned in a segment of 1-250 mm from the tip, wherein the diameter of the single aperture is between 70% and 120% of the inner diameter of the outer tube [1], or in case of several apertures, for each aperture 30-60% of the inner diameter of the outer tube, wherein the outer diameter of the inner tube is between 0.6 mm and 2.0 mm (F2 to F6), the outer diameter of the outer tube is between 1.3 mm and 3.6 mm (F4 to F11), and the distance between the outer wall of the inner tube and the inner wall of the outer tube is between 0.1 mm to 3.0 mm.

12 Claims, 13 Drawing Sheets

Junction segment (12)

aspiration, target vein collapse (12)

sclerofoam injection vein spasm, foam aspiration

Inner tube loaded with glue (12)

gluing glued segment (12)

Figure 1A:
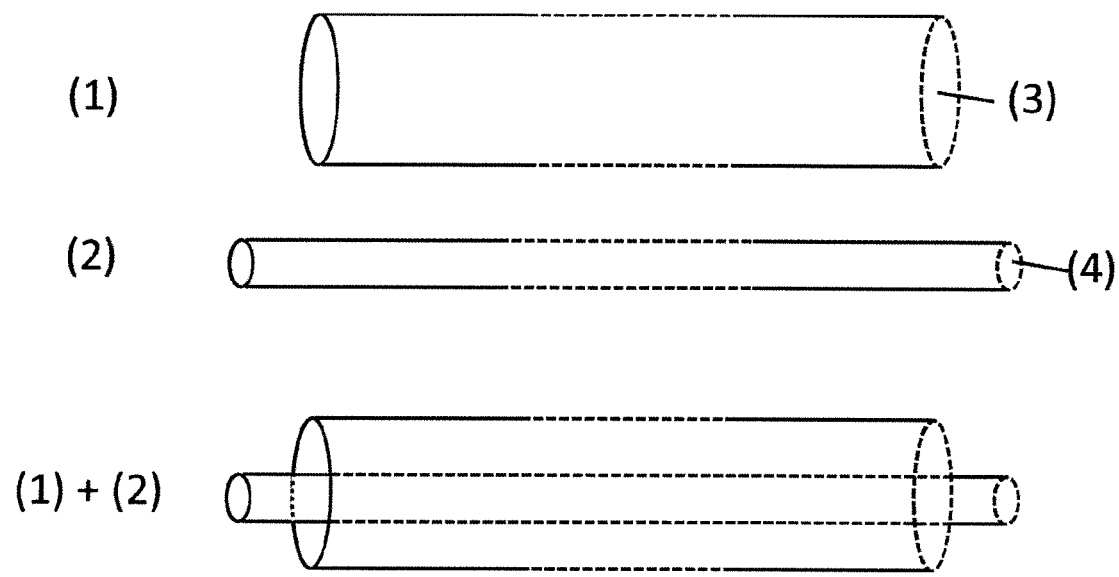

Catheter withdrawn, vein closed aspiration, target vein collapse

Foam injection vein spasm, foam aspiration glued segment

Catheter withdrawn, vein closed, vein size reduced

METHOD AND DEVICE FOR TREATING VENOUS INSUFFICIENCY AND VARICOSE VEINS

This application is a U.S. National Stage of PCT/EP2013/058066, filed Apr. 18, 2013, which claims priority to European Patent Application No. 12165246.5, filed Apr. 24, 2012, the disclosures of each of which are incorporated herein by reference in its entirety.

FIELD OF THE INVENTION

The present invention is in the field of medicine, more in particular in the field of vein diseases such as venous insufficiency, varicose veins, ectasias or aneurysms in humans and animals. The invention is also in the field of pharmaceuticals and medical devices for treating such diseases.

BACKGROUND

Blood vessels in humans and animals are grouped as arterial and venous, determined by whether the blood in it is flowing away from (arterial) or toward (venous) the heart. Veins collect blood from organs, muscle, connective tissue and skin. Venous blood has a low content of oxygen and nutrients, but enriched in carbon dioxide and other components, such as waste products.

Caused by acquired functional weakness due to lack of activity or by congenital defects, a large number of people show venous congestion in the legs. Congestion means a presence of blood above the physiological level. If no change in habits occurs, congestion turns into insufficiency within few years. Insufficiency means that vein valves become incompetent, resulting in a reversed blood flow. In a vicious circle insufficiency further increases venous blood congestion, and the disease increases with time.

Varicose veins develop from insufficiency. They are superficial veins which have been stressed by an overload of blood for years and therefore show large diameters and a tortuous course. Incompetent leg veins are found in 21-25% of people aged 35 or above, and spider veins even in 50% (Maurins et al. Distribution and prevalence of reflux in the superficial and deep venous system in the general population—results from the Bonn Vein Study, Germany. Journal of Vascular Surgery, Vol 48, Issue 3, September 2008, 680-687).

Beside the cosmetic issues, insufficient and varicose veins lead to major complications, due to the congestion and the poor circulation through the affected limb. The complications comprise pain, heaviness, inability to walk or stand for long hours, skin inflammation, skin damage predisposing skin loss or skin ulcers especially near the ankle, usually referred to as venous ulcers, severe bleeding from minor trauma, blood clotting within affected veins (thrombophlebitis, thrombosis, embolic events). Even the development of carcinoma or sarcoma in longstanding venous ulcers has been reported in over 100 cases. The rate of malignant transformation is reported as 0.4% to 1% (Goldman M. Sclerotherapy, Treatment of Varicose and Telangiectatic Leg Veins. Hardcover Text, 2nd Ed, 1995).

For dilated veins, surgical removal of the target structure, e.g. varicose veins, has been a widely used therapy for decades. However, like all surgical treatments this may be accompanied by several, partially serious adverse effects, i.e. damaging of adjacent arteries, nerves or lymphatic vessels, generation of wounds and cicatrices, wound infections, or intolerance of the patient for narcotic drugs. Furthermore, the tissue damage going along with every surgery, in particular in junction regions like the groin or the poplitea seems to induce the growth of new, but diseased veins.

As an alternative to surgical removal, different ways of endovenous closure methods have been developed. The term endovenous means, therapy is performed by access through the venous system, and within the diseased vein. The aim of these methods is the permanent closure of the treated vein or vein segment. The effect may be obtained by thermal treatment (e.g. by laser, radiofrequency, steam), or by injection of chemical agents (fluids, foams). Due to the use of catheters and probes, thermal treatment is restricted to relatively linear vessels while chemical agents may also reach curved and tortuous segments, or branched (reticular) veins.

For many applications, today's catheter technique is not yet satisfactory. For example, techniques requiring saline rinsing do not offer particular rinsing catheters. Instead, physicians have to use haemostatic sheaths built for arterial access. Another example are techniques profiting from the absence of blood in the veins to treat, like sclerotherapy, 1000-1600 nm endovenous lasers, steam or radiofrequency. For these methods, no particular techniques to achieve absence of blood have been presented so far. Even for meanwhile wide spread foam sclerotherapy no particular foam delivering catheter is commercially available. Significantly, by using simple tube-like catheters, incidental foam misplacements are frequent, and success rates cannot compete with those of thermo-occlusive techniques.

Few other treatment modalities have been reported, relating to other types of venous disease, like varicose veins of the esophagus which are a consequence of liver disease caused vein congestion, with the complication of dangerous bleedings. These bleedings are life-threatening. Emergency examinations are performed by endoscopy (large steerable tubes with fiber optic), and working channels of these endoscopes have been used to inject sclerotic agents or glues. The indication is to stop the bleeding, not the treatment of an insufficiency. These modalities are not endovascular and cannot be applied on peripheral veins.

The use of medical glues in peripheral veins via simple tube like catheters has been evaluated by the inventor since 2007. However, the distribution of glue within the vein was irregular with parts spared from glue and parts with accumulation of too much glue, and therefore not satisfactory. Furthermore, the application depend on external manual compression which excluded the use for the most important, but deeper junction regions of the saphenous veins, or perforator veins (veins connecting superficial vessels to the deep venous system). If properly feasible, gluing could combine vein closure with immediate diameter reduction.

The effect of all the named endovascular methods applied to peripheral veins is to permanently denature functional proteins in the innermost tissue layer (the endothelial cell layer). Said denaturing process triggers the aggregation of blood cells, in particular thrombocytes, at the vein wall. It is a kind of artificial thrombosis. In contrary to incidental thrombosis which may be hoped to resolve, in the therapeutic approach the aim is to completely denaturize all the endothelium in the segment to treat. Only parts of the vessel wall sufficiently reached by the thermal or sclerotic effect can be expected to close permanently, as undamaged endothelium will revitalize and lead to recurrent pathologic blood flow.

All endovenous procedures are associated with a local vein spasm, due to effects passing the endothelium layer and reaching the muscular layer. Spasm means a contraction of muscular cells. The vein spasm triggered by endovenous techniques is in general not lasting longer than minutes above the active presence of the modality. However, it would be desirable to maintain the spasm or permanently the vein size reduced by spasm, as one important aim is to decrease the vessel diameter. A real initial shrinking will only be obtained, if the effect reaches deep into the muscular layer with a permanent shortening of fibers. On the other hand, with increasing effects on the muscular layer the danger of vein perforation increases, and so does pain during and after treatment as there are only micrometers distance to the innervated outer wall layer (called adventitia). Therefore, all sclerosant or thermo-occlusive techniques do not initially achieve a sufficient lumen reduction. The vein spasm itself deserves attention, as it is not just an incidental side effect but could be used as a main step for a more effective vein treatment.

Known liquid sclerosant drugs are e.g. alcohols with detergent properties like polidocanol or sodium tetradecyl sulphate. In the eldest modality, the liquid sclerosant drug is injected directly into the vessels. Due to its high fluidity the liquid sclerosant drug flows with the blood stream and quickly mixes with blood, soon reaching ineffective dilutions. Protein bindings additionally limit the effect of fluid sclerosant agents.

In order to circumvent some drawbacks of the liquid sclerosant drugs, one usually makes a sclerosant foam by mixing the liquid sclerosant drug with a gas. The resulting sclerosant drug foam is injected into the target structure, e.g. the varicose vein. For foaming the sclerosant drug (e.g. Sodium Tetradecyl Sulfate or polidocanol) is mixed with sterile air or a physiological gas (carbon dioxide) in a syringe or by using mechanical pumps.

Foaming increases the surface area of the drug. Due its higher viscosity, the sclerosant drug foam is more efficient in causing sclerosis than the liquid sclerosant drug (thickening of the vessel wall and sealing off the blood flow; Yamaki et al. (2004) Comparative study of duplex-guided foam sclerotherapy and duplex-guided liquid sclerotherapy for the treatment of superficial venous insufficiency, Dermatol Surg 30 (5): 718-22; Hamel-Desnos et al. Evaluation of the Efficacy of Polidocanol in the Form of Foam Compared With Liquid Form in Sclerotherapy of the Greater Saphenous Vein: Initial Results Dermatol Surg 29 (12): 1170-1175 (2003)).

All foams, regardless of how they are produced, have several disadvantages: If injected fast enough, foam may replace blood for a certain time, varying from seconds to a few minutes. In this time, the contact to the vein wall is more intense than in case of a liquid bolus just passing by. The chemical reaction of the sclerosant on the endothelium (innermost wall layer) will expand to the media layer and trigger muscular spasms. Therefore, the vein will shrink by spasm to a percentage of 5-80% of its original diameter. The spasm will displace a majority of the foam to neighboring vessels, and at the same time by increased flow resistance prevent the treated segments from relevant perfusion. The vein musculature will relax after 5-60 minutes, and remainders of foam will then be washed away. When the vein spasm vanishes, blood returns to the target vessel. Although by external compression (stockings, bandages) the amount of blood returning to the treated vein can be reduced to some extent, it cannot be completely avoided. The target vein cannot be adjusted to the desired diameter. This is in particular true for deeper veins, in order to compress them effectively one must compress the nearby main veins at the same time, with the consequence of distal congestion. Nevertheless, foam sclerotherapy seems to be an important modality as it is applicable in almost every diseased vein as far as the region is accessible by catheter, and it does not require tumescent or even general anesthesia.

Another way of reducing the amount of blood in a vein during or after endovenous treatments could be to simply lift the leg above heart level. However, this works temporarily and it is not very effective as there is always collateral blood flow due to continuous arterial inflow. A short-term leg elevation will furthermore delay the treatment, increasing the risk of thrombosis. A long-term elevation of the patient's leg (hours to days) would mean immobilization, requiring anticoagulation (e.g. injections of heparin). Some advantages of endovenous treatments, in particular the immediate mobilization and ability for work and sports would be counteracted.

If all the endothelium has been completely denatured, its ability to prevent blood cell adhesion is lost. Therefore, the vein will close within the following 1-24 hours by thrombosis. Some methods are able to achieve immediate thrombosis (e.g. laser 750-1000 nm), but they fail in achieving initial lumen reduction, furthermore later-on lumen filling by blood amounts transversing by opened vasa private, or side branches. With these effects the vein diameter increases, marginal flow may be detected for a few days, but the vein will then close for a longer period, or forever. At this point of terminal vein closure, there is no more perfusion in this vessel, and the pathological backward flow is eliminated. This is the same hemodynamic effect like achieved by surgery ("elimination of reflux"), and it is the main endpoint of treatment quality.

In contrary to surgery, the vein is still in place. For optimal results, it should now be neither visible nor palpable. The patient should not feel its existence when moving or at rest. However, this goal is not achieved with today's techniques.

When, after sclerotherapy or thermo-occlusion of the described kind, blood re-enters the target vein once the spasm is gone, the total amount of clotted blood contained in the vein will determine the duration and symptoms of the reorganization process. Clotted blood within the vessel will have to be removed by metabolization, leading to a change from thrombus to shined connective tissue. As a fact, the incidence of unwanted side effects like painful inflammations, brownish discolorations, long-lasting indurations and visible varicose veins rises with the vein diameter at the time of terminal thrombotic closure.

In clinical practice the majority of sclerotherapies and also thermo-occlusive treatments are not complete in the sense of total circumferential endothelium denaturation. For example, in case of slow injection, and also in case of complex and tortuous varicose formations which limit the injection velocity, foam floats on top of the blood instead of replacing it. Only partial denaturation of the endothelium is achieved. Trials have shown that turning the patient does help. In the case of incomplete endothelium destruction, due to vital endothelium isles painful phlebitis is frequent, and therefore the closure is not stable and shows early relapse.

Hence, sclerosant drug foams of prior art are not well suited for treatment of larger target structures, as they frequently cause painful inflammatory reactions or lack of lasting effects with respect to the occlusion of the target structures.

Other means of non-surgical venous closure, such as radiofrequency, laser or steam (summarized as thermo-occlusive techniques) show this disadvantage in a lesser, but still significant way. They all may achieve a closure of the target vein, but none of them is capable of immediately and sufficiently shrinking the vein. This is in particular true for veins with big diameters (>12 mm). The bigger the vein's diameter, the higher the risk is of leaving vital endothelium isles due to insufficient energy transfer. Besides this, thermo-occlusive techniques require local anaesthesia and cooling fluids which have to be injected in a time consuming manner. Veins with large diameters will, when collapsing, tend to form folds in which endothelium is protected from laser, steam or radiofrequency energy. Furthermore, the effects of these techniques will not include side branches and perforator veins, leaving vital endothelium and therefore incomplete results and sources of relapse.

While thermo-occlusive methods are able to work with a precision of 1-10 mm, sclerotherapies are less precise as fluids or foams will propagate depending on the injected amount, and on the induced spasm which will decrease the lumen and spread the sclerosant towards more or less distant areas. Even very experienced physicians can not control the effect of sclerosants with a precision less than several centimeters. Side effects are thrombosis (1-3% of the cases), phlebitis (3-18%), occlusion of healthy veins (usually without symptoms and thus greatly underestimated). The lack in precision also leads to frequent failures, thus, sclerotherapy is world-wide said to be a multiple-step treatment. The reimbursement is low.

It would be advantageous to have means for instantaneous and permanent closure of diseased veins, also providing an immediate and permanent lumen reduction.

DESCRIPTION OF THE INVENTION

By treatment of dilated or insufficient veins with a sclerosant drug or thermo-occlusive techniques, no sufficient immediate shrinking and closure of these veins will be achieved. The veins will frequently show painful inflammatory reactions, delayed resorption, indurations and discolorations and incomplete results with recurrent backward blood flow.

Sclerosant foams are commonly applied via cannula, and rarely via a catheter. In fact, there is no catheter product existing in particular designed for venous foam applications. As veins are tubular organs with very thin and soft walls, in contrary to arteries which have thick walls. To avoid unwanted lesions in these vulnerable structures venous instruments have to be much softer as for arterial vessels.

The inventor found that the optimal catheter for foam application should have a large lumen-to-wall ratio, which means a thin wall and a wide lumen, and a non-sticky wall, offering enough stability to forward the catheter even without guide-wire, and at the same time be soft and flexible enough to follow even narrow curves and to exclude rough force transmission which could harm healthy vessels.

Foam stability is affected when pressed through narrow cannulas or catheters, as some bubbles will collapse. The desired displacement of blood by foam is more precise when the feeding instrument is large in diameter, reaching almost up to the diameter of the target vessel. Otherwise, a jet of sclerosant medium from a small diameter tool into a much larger vessel will be rapidly diluted and therefore be limited in its desired medical effects.

In earlier laboratory setups (glass tube models) the inventor showed that using common cannula or small catheter tools in horizontal target vessels with at least the four fold cross section area compared to the tool lumen, foam injections performed via hollow needles up to 0.6 mm inner diameter in veins of 8 mm have to be performed at least at 2 $cm^3$/s to completely replace the blood column. Otherwise, the foam would partially float on the blood and not reach its medical aim. However, these high-speed injections easily lead to overdosage, involving healthy vessels with the danger of thrombosis and phlebitis. (see Injektionen von Polidocanol—Schaum: Simulationen in einem Röhrenmodell. Ragg J. C. et al., Phlebologie 4-2008 A11-055, Jubiläumskongress 50. Jahrestagung der Deutschen Gesellschaft für Phlebologie 2008, Bochum).

The inventor has solved the above problems as best possible by providing for the following:

The invention relates to a double-tube injection and aspiration catheter device for endovenous use. Endovenous means that the device is introduced to a vein, advanced within the vein to a target segment, and its effects applied from within the vein (FIG. 1b). The catheter device according to the invention offers options to 1) modify the size of the target vein during treatment, either temporarily decreasing the diameter by evacuating blood, fluid agents, foams or gases, or temporarily increasing the diameter by injection of fluid agents, foams or gases; 2) to administer fluid agents, foams, gases or glues, furthermore 3) to provide effective point wise or segment wise gluing of veins, 4) to combine gluing with sclerotherapy in one single treatment, 5) to simplify and optimize thermo-occlusive methods by providing simultaneous evacuation, and 6) to allow combined treatments with sclerotherapy and/or thermo-occlusive methods, and/or glue, in one single session with immediate and permanent closure and lumen reduction.

Figure 1B:
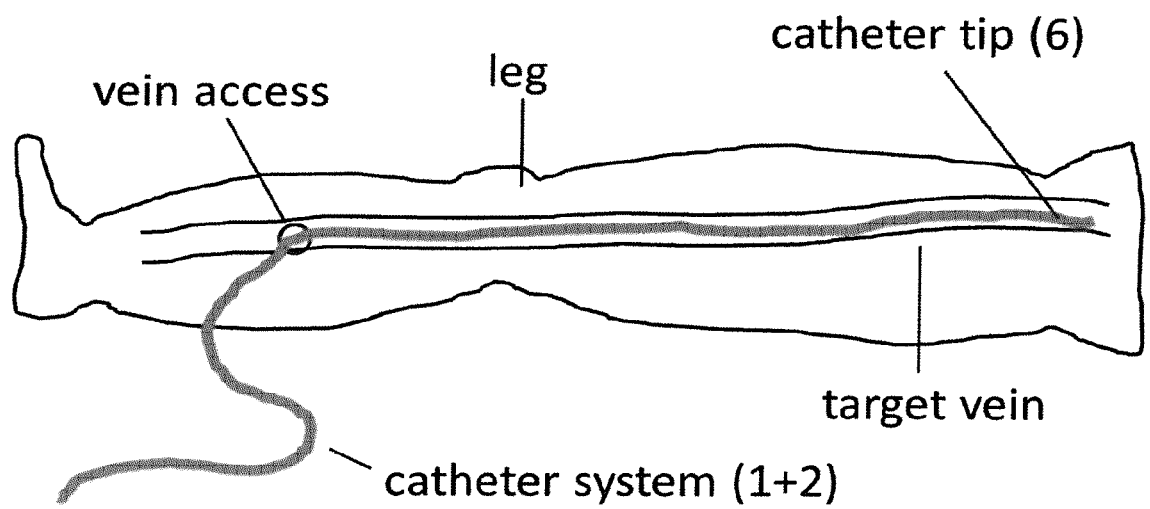

The double-tube injection-evacuation catheter device comprises two plastic tubes, one larger outer plastic tube [1], containing a smaller inner plastic tube [2] (FIG. 1a). The two tubes are spaced apart to provide room for the injection or evacuation of larger quantities of substances via the outer tube. All tubes have openings at both ends and all are fully relocatable and demountable (FIG. 1a). Herein, a larger tube is interchangeably used with outer tube. Inner tube is interchangeably used with smaller tube. Some embodiments make use of an additional tube. The additional tube is also termed covering tube.

A catheter is a medically used tube for the transportation of fluids, gels, foams, pulps or gases. A tube is defined as a cylindrical hollow body with a length much larger than its diameter. In this application the relation of length to diameter is at least 50. Herein, the terms catheter and tube are interchangeably used.

Plastic means a plastic material of a wide range of synthetic or semi-synthetic organic solids that are mouldable. Plastics are typically organic polymers of high molecular mass, but they often contain other substances. They are usually synthetic, most commonly derived from petrochemicals, but many are partially natural.

The double tube injection-evacuation catheter device is for application in veins of different sizes (preferred diameter of veins: 3-60 mm). For large veins, a larger system will be required, and for small veins, a smaller catheter combination. It is preferred that the vein to be treated has a diameter between 1.5 and 2 fold of the outer diameter's catheter. Examples are given in Tab. 1 below.

Due to the investigation of the new catheter it was found that a proper displacement of blood by foam sclerosant may require a catheter lumen of at least 25% of the target vessel cross section area.

Another important feature is at least one sidehole. When distributing a foam through a tube or a catheter, there is a resistance to be overcome, increasing in a linear way with the tube length. If the tube is equipped with a side hole, the injected substance may take the way of lesser resistance for its exit. The larger the side hole, the lesser the resistance. The required size of the side hole depends on the viscosity of the foam, its bubble size, and stickyness. It furthermore depends on the space between catheter and vein, as also this way of distribution is correlated to a flow resistance decreasing with size. The aim for optimal foam deployment is to exit 100% of the foam via side hole.

The inventor further found that for optimal foam injection the outer diameter of the catheter should be 0.5-0.66 fold of (native or adapted) vein diameter (VD). The vein diameter VD is measured in the patient's treatment position. The vein diameter will change according to the inclination degree: A vein is at maximum diameter in a standing patient (which is never a treatment position for foam sclerotherapy), and at a minimum when the vein is elevated above heart level.

If the foam is applied via sidehole, it will fill the space between catheter and vein wall. After foam delivery via side hole, the foam column will propagate slowly and well steerable towards the distal target end (e.g. vein junction). After reaching the target end with the foam, the catheter is withdrawn until the side hole reaches foam free space, and then injection is continued while slowly further retracting the catheter until the proximal target end is reached.

The inventor further found it helpful to adjust the target vessel, if not fitting in native status, to a diameter of 1-3 mm larger than the catheter OD. In this case, a foam injection will always exit the side hole and surround the catheter from all sides, forming a distinct line towards the blood. This line is well recognizable in ultrasound and can be used to carefully approach junction zones without overdosage or floating effects.

The space between catheter and vein wall is much smaller than the vein lumen without catheter. It saves up to 75% of the foam quantity if this technique is chosen. After foam delivery, a vein spasm will be induced in the foam-filled segment. The spasm reduces the diameter by 50-90%. If injecting via simple cannula, the large foam volume will be displaced by the spasm in large quantities. If the catheter according to the invention is used, its retraction adapts the available space to the given foam quantity. When withdrawing the catheter, the amount of foam applied will just fill the collapsing lumen. It could be shown that foam displacement by spasm was reduced by the described catheter techniques by 20-80%, depending on the ratio of catheter diameter (OD) and vein diameter (VD).

For practical use, catheter access sites up to 2.8 mm in diameter may be regarded as acceptable. It is not necessary to have larger tools, as the diameter of the target vessel can be adjusted with several methods: 1) Lifting the leg will empty the veins, and their diameter will decrease. 2) aspirating blood from the vein will have the same effect, as long as there is no collateral inflow. 3) surrounding the vein with injectable fluids or gels will compress its diameter.

The only reasons to use catheters much smaller than the target vessel could be: 1) easier introduction through skin, tissue and vessel wall at the puncture site, 2) easier closure of puncture site after the intervention with lesser risk of bleedings. However, the demands of proper foam delivery with maximum effect (reliable obliteration) and maximum safety (no side effects like thrombisis, phlebitis, embolism) are of priority.

The diameter of the inner tube may be between 0.6 mm and 2.0 mm (F2 to F6) or even between 0.2 and 2.0 mm, preferably between 0.4 and 1.0 mm, the diameter of the outer tube may be between 1.3 mm and 3.3 mm (F4 to F10) depending on the diameter of the vein to be treated.

The distance between the outer wall of the inner tube and the inner wall of the outer tube is preferably 0.1 mm to 3.0 mm. It is preferably chosen in a way providing a large free space between the fully mounted tubes of 33-66% of the outer tube's inner cross section to allow easy evacuation of blood or substances as well as easy deployment of sclerosant or rinsing fluids.

Figure 2:
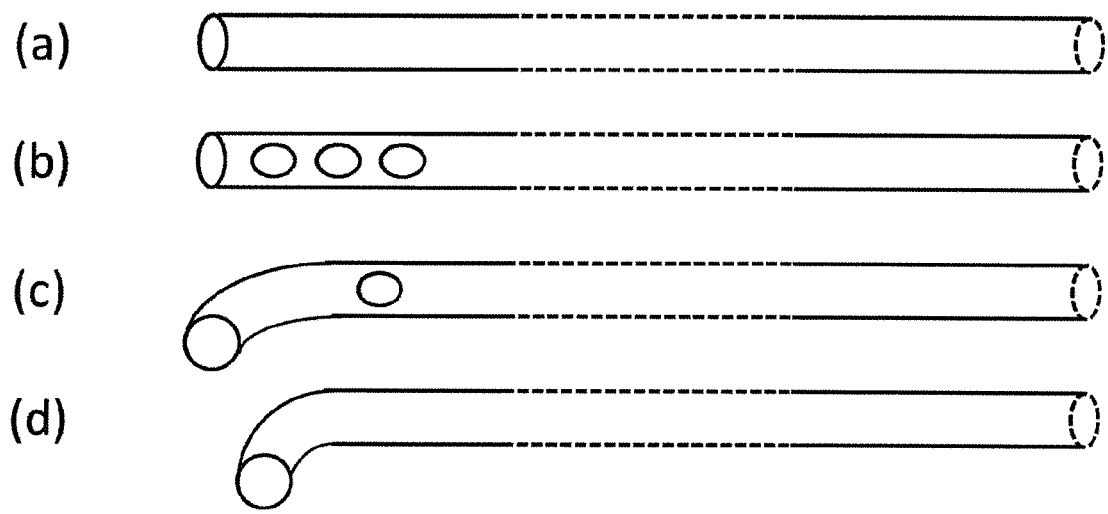

The inner tube mainly serves to deploy medical glue. When gluing tissue, it is best to use as little glue as possible. Therefore, a small lumen of the glue delivering catheter helps to achieve a precise dosage of small amounts of glue. However, the lumen must also be large enough to transfer the required amount in a reasonable time. In this invention, the lumen size of the inner catheter was found for gluing to be preferably 0.4-1.0 mm. The shape of the inner tube may be straight, or slightly bent (5-20 degrees) to steer along curved vessels or navigate through junctions, or it may also be bent unto or even above 90 degrees to navigate through junctions with such angles (FIG. 2). For deployment of substances, the inner catheter may have one or several side holes to achieve uniform placement of the substance along a segment to treat. The inner tube may have a tempered tip for easier introduction. The inner tube may also, alone or with a guide-wire support, serve as an introduction aid like a stiff guide—wire: If introduced to a target vein as the first part, larger parts of the catheter system may be advanced by pushing them along the inner tube. It may furthermore serve to deploy fluid agents (sclerosant), or serve as an outlet valve during injection or evacuation actions of the outer tube.

The outer tube serves to 1) evacuate blood from the target vessel seconds before application of glue or glue compositions, sclerosant agent, or the application of thermo-occluding techniques; 2) maintain evacuation and/or negative pressure during these applications; 3) administer saline or other liquids for rinsing if required by the used technique; 4) administer foam sclerosant; and 5) evacuate sclerosant.

Figure 3:
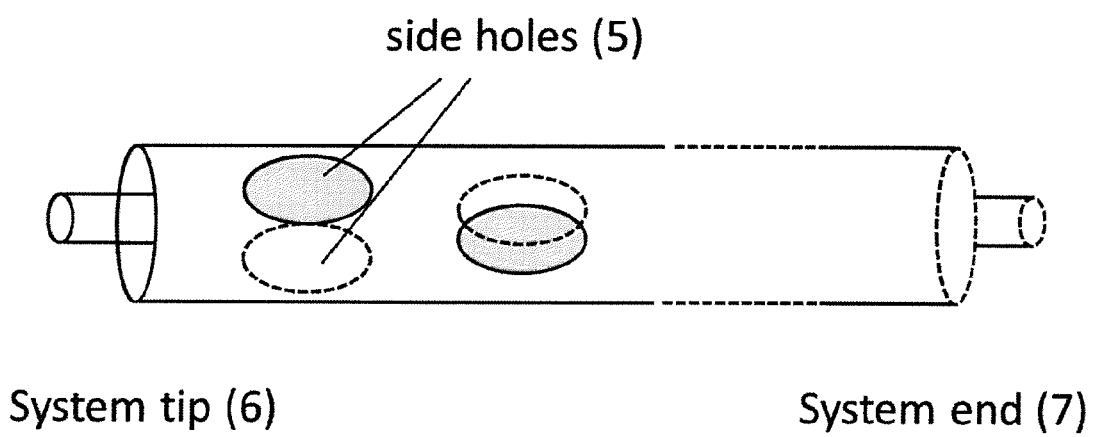

To fulfil these purposes in different anatomic situations, in a preferred embodiment there is at least one hole [5] provided in the wall of the outer tube, but more preferably 2-20 holes (FIG. 3). A single hole is located at a position of 5-40 mm from the tip. Multiple side holes are beginning in a position of 5-40 mm from the tip and ending at 60-250 mm from the tip. The size of a single side hole is equal to 80-120% of the outer tube's lumen, or, in case of multiple side holes, each varying between 30 and 60% of the outer tube's lumen. Lumen means the free inner diameter. It defines the space available within the tube.

Figure 4:
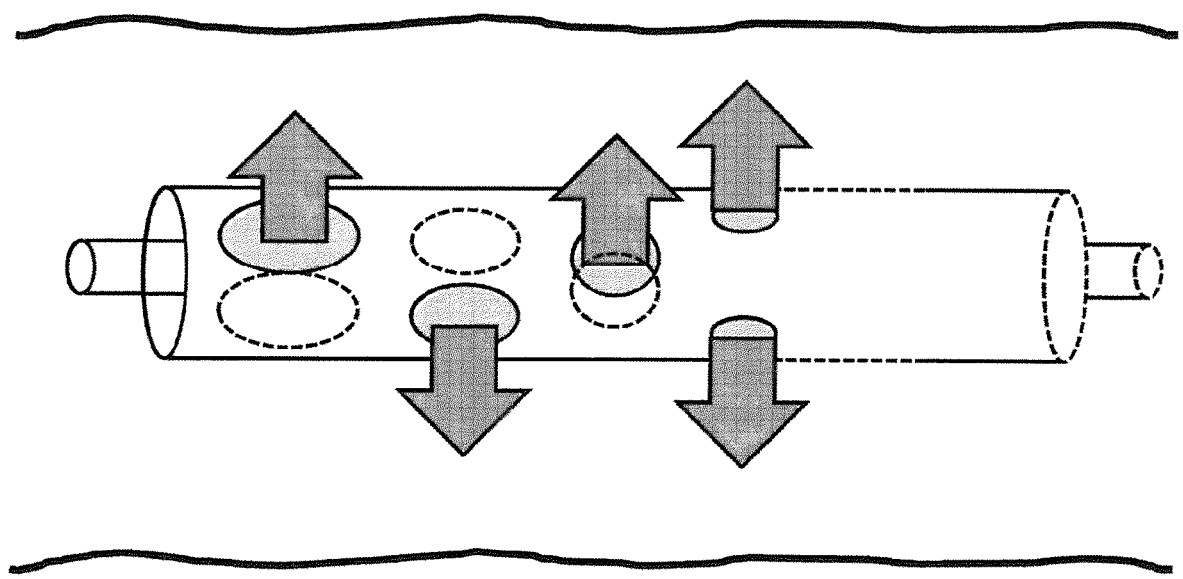

The side holes may be different in size, shape and distribution. For example, the holes may be round, elliptic, or rectangle. The most proximal side hole may be larger than the others (FIG. 4). The inventor even found that the optimal size, shape and distribution of side holes may depend on the agents to be administered, for example sclerosant foams of high viscosity may require larger side holes.

Figure 5A:
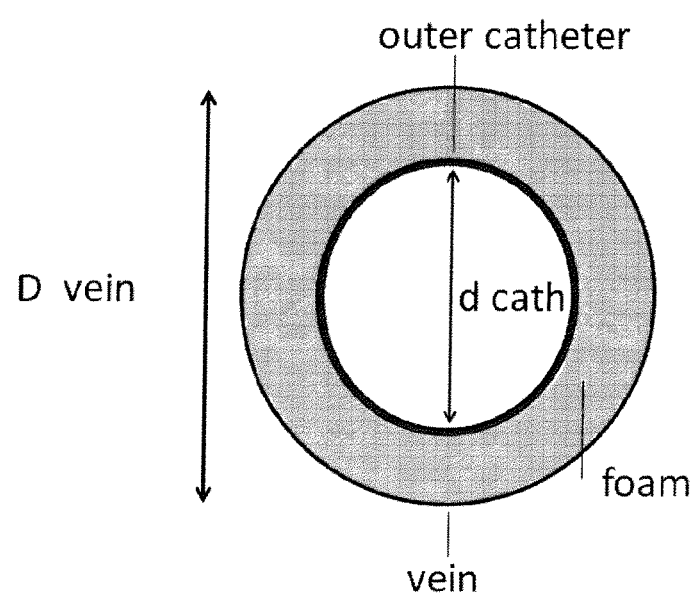

A foam deployment for sclerotherapy is regarded as optimal if the substance spreads uniformly around the tool, and keeps a uniform and distinct front line during injection to achieve precise placement (FIG. 5a,b).

According to the experience of the inventor, using the outer catheter with 4-12 side holes for the application of polidocanol foam, a longitudinal precision of 0.5 cm could be obtained. During the evaluation, more unexpected properties became apparent: The optimal ratio for precise sclerofoam treatment is met when the catheter volume along a foam quantity is equal to the volume of deployed foam (FIG. 5a). In this case, withdrawal of the catheter will provide exactly the space required to take the total foam quantity when the drug-triggered spasm contracts the vein. Hence, foam will not spread above the target zone. Furthermore, the volume of the catheter will reduce the quantity of foam sclerosant required to fill the vessel.

Figure 6A:
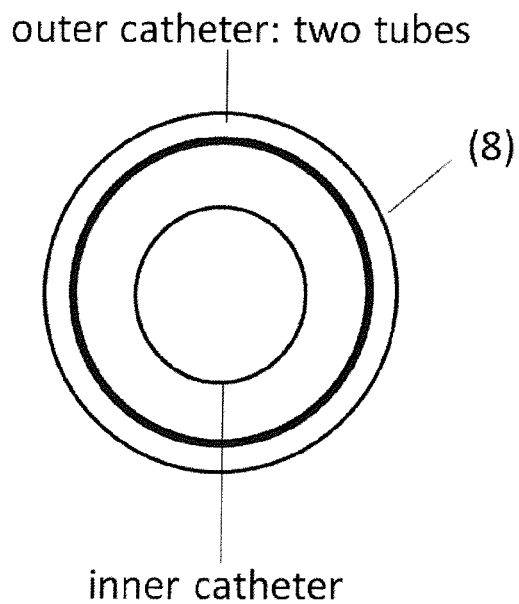

The side hole function can be used in a further way, if an additional relocatable tube [8], (FIG. 6a-e), is placed around the outer tube. The distance between the additional tube and the outer surface of the outer tube is 0.05-0.5 mm, it depends on the tubes surface and friction properties. The preferable distance is defined by the necessity to allow sliding of the outer catheter within the additional tube, but exclude undesired movements. The additional tube is always shorter than the outer tube, preferably 5-90 cm, defined by the demand to slide this tube to a position uncovering all side holes. The diameter of this additional tube [8] is always larger than the outer tube [1] (FIG. 6a), but the wall thickness should be rather small as it enlarges the diameter of the whole system and thus the required tissue hole at the entry site. The wall strength is chosen in a way providing safe closing and opening function of the side holes, preferably it is 0.2-0.4 mm.

Figures 6B, 6C, 6D:
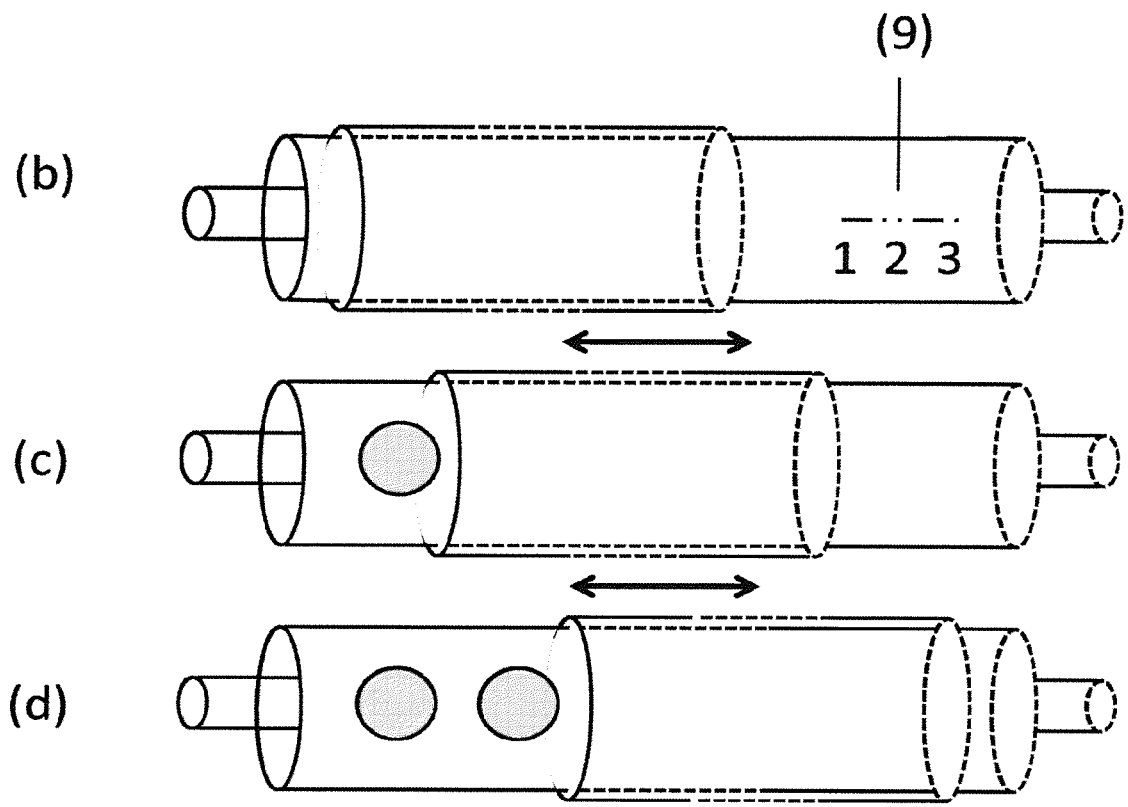
Figure 6E:
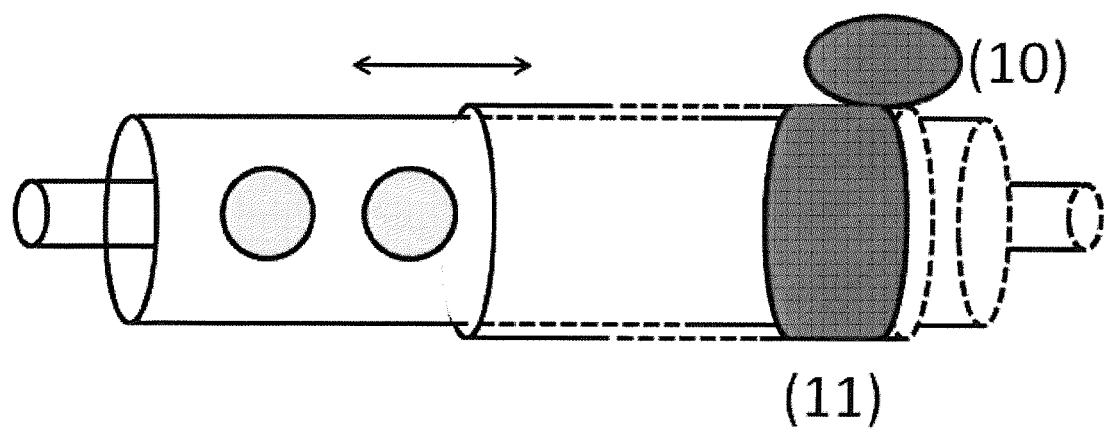

The tubes [1, 8] (FIG. 1a) work together as a functional unit: The additional tube [8] fulfils the task to cover or to uncover the side hole(s) of the outer tube (FIG. 6). In one position, all side holes are covered (FIG. 6b). In another position, one side hole is opened (FIG. 6c). In another position, more ore all side holes are opened (FIG. 6d). The additional, i.e. covering, tube may have a grip [10] or handle [11] at the proximal end for easier movements (FIG. 6e). There also may be markings or other signals or signal devices at or within one tube or both tubes to determine the status of the outer tube's side holes, while the system is positioned within the patient's body.

The length of the outer tube is 6-120 cm. The inner catheter is 1-20 cm longer than the outer tube (7-140 cm). If used for guidance purpose, it may be up to 260 cm in length. To adapt the length after introduction, the inner tube may be suitable for cutting. The material of the tubes should be smooth, flexible, and non-sticking. It is therefore preferably chosen from the group of PTFE, PFA or FEP.

The invention relates also to a composition comprising (a) a pharmaceutically acceptable glue, wherein the glue can polymerize on contact with water, tissue fluids, blood or blood fractions; and (b) a medical gas acceptable for use within veins, like oxygen, carbon dioxide or mixtures thereof, for use with the double-tube catheter. A composition herein may be a mixture but is also defined broadly and relates to two different substances loaded within one chamber or catheter. This is important as, e.g. gas and glue may be separated and applied in form of separated boli.

It relates also to a kit comprising (a) a pharmaceutically acceptable glue, wherein the glue can polymerize on contact with water, tissue fluids, blood or blood fractions, and optionally (b) a medical gas, or compositions of glue and medical gas, and/or (c) a sclerosant drug.

It also relates to a kit comprising (a) a pharmaceutically acceptable glue, wherein the glue can polymerize on contact with water, tissue fluids or blood or blood fractions and (b) a medical gas or compositions of glue and medical gas, and/or (c) a sclerosant drug, and/or (d) the described double-tube injection-aspiration catheter.

It furthermore relates to a kit comprising (a) a pharmaceutically acceptable glue, wherein the glue can polymerize on contact with water, tissue fluids or blood or blood fractions and (b) a medical gas or compositions of glue and medical gas, and/or (c) a sclerosant drug, and/or (d) the described double-tube injection-aspiration catheter, and/or e) an introduction device and a hydrophilic guide wire, and/or f) a probe for the application of radiofrequency or laser light to the target vein.

It also relates to a kit, wherein the catheter system includes chambers, cartridges or syringes to contain or deploy glue, sclerosant, foam, gas or blood, and a kit wherein the catheter system includes mechanic, pneumatic, hydraulic or electric/electronic means to support or perform injection and/or aspiration.

DETAILED DESCRIPTION OF THE INVENTION

By treatment of dilated or insufficient veins with sclerosant drugs or thermo-occlusive techniques, no sufficient immediate shrinking and closure of these veins will be achieved. The veins will frequently show painful inflammatory reactions and indurations for days to weeks after treatment with delayed resorption and discolorations. Furthermore incomplete results and relapse may result.

The inventors have discovered that by use of the presented double-tube injection-aspiration catheter system, a glue or glue composition as outlined herein can be brought into a vein in a way effectively connecting the vein walls. The injection-aspiration catheter system furthermore allows enforcing the gluing action by using a sclerosant-mediated vein spasm for compression during the gluing phase. It also allows combining gluing with sclerosant agents, or thermo-occlusive endovascular methods, in one single procedure. This way the effects of endothelium-aiming treatments can be amplified by use of the double-tube system, offering simultaneous evacuation of blood or fluid rinsing.

Immediate closure of diseased veins is achieved and the vein size is permanently reduced at the same time so that the medical aim of eliminated reflux and cosmetic aim of non-palpable and non-visible residual is fulfilled. According to clinical experience, an immediate lumen reduction of 50-90% is sufficient.

The main use of the new double-tube injection/aspiration catheter is to achieve permanent occlusion by catheter—modified sclerotherapy, while obtaining immediate closure by connecting the vein walls by gluing. The outer catheter serves to aspirate blood from the target vein or target vein segment, to administer sclerotic agent, to aspirate sclerotic agent, and to provide exsanguinations and negative pressure during glue is applied via the inner catheter while the sclerosant—triggered spasm additionally compresses the vein walls. The inner catheter serves to deploy glue, but also may work to administer fluid sclerotic agent, or as an outlet.

Typical steps of the application are (FIG. 8):
a. Positioning of the system with a distance to the spot to start closure [12], e.g. 0.5-20 mm.
b. Positioning of the inner catheter distal to the spot to start closure [12], e.g. 0.2-10 mm.
c. Exsanguination by aspiration of blood via the outer catheter [1]. Vein will collapse.
d. Administration of sclerotic (foam) agent via outer catheter until edge of treatment segment is reached. Residence time 60 s.
e. Aspiration of sclerotic agent (and eventually blood) to re-establish an empty and collapsed vein.
f. Inner catheter [2] is loaded with glue (as a fluid, gel, or foam), or gas-glue-gas portions
g. While maintaining negative pressure, glue or gas-glue-gas-portions are administered. Negative pressure maintained for 30-120 s.
Glue connects the vein walls irreversibly.

h. Withdrawal of the system to next application position, which is recommended to be at least 2 times and maximum 10 times the veins original diameter (as measured in the patient standing) distal to first position.
i. Repetition of the procedure until completion of the vein segment to treat.

The effect of successful gluing may be proven by injection of gas, foam, or fluids, but the glue will stick better if left unstrained for 10-60 minutes. Clinical proof of successful gluing is given by the parameter of vein diameter remaining small, or even deteriorate.

For use in superficial, tortuous and smaller varicosities the system is used in a modification combining an outer catheter of F 2-F5, length 6-20 cm, with a double- or triple-cut tip hollow needle of 0.5-1.6 mm outer diameter. Optional, the hollow needle may carry a transparent aspiration chamber to indicate blood contact during introduction. The system is suitable for direct puncture of the target vein, and for intraluminal advancement guided by ultrasound imaging. After reaching the desired position, defined by introduction of the whole catheter length, or by reaching anatomic landmarks, or by too sharp bends which can not be passed, the hollow needle is exchanged for the inner catheter. The rest of the procedure is a) aspiration of blood contained in the vein until exsanguination, administration of sclerotic agent (preferred: foam), residence time of e.g. 60 s, aspiration of sclerotic agent and blood remnants, administration of glue or gas-glue-gas portions while maintaining negative pressure.

Besides these main purposes, the system allows the application of other endovascular modalities while leaving the outer catheter in place:
a. Application of laser radiation, radiofrequency, saturated steam or other endovascular modalities during exsanguination (F5-F9)
b. Application of laser radiation, radiofrequency, or other endovascular modalities during flushing with saline (F5-F9)
c. Application of particular shaped or shapeable probes for direct or selective treatment of side branches or perforator veins (veins connecting to the deep venous system)
d. Combining thermo-occlusive methods with sclerotechniques, allowing the administration of sclerofoam via the outer catheter while thermo-occlusive probes are in place.
e. Combining thermo-occlusive methods with gluing, e.g. closing junction segments with well proven laser or radiofrequency, and treating of other segments with combined sclerotherapy and gluing by use of the same catheter system.

The application of glue in the described manner does not depend on any external manual or mechanical compression. It is therefore applicable for any vein in the body, from the skin surface down to the innermost veins of the body.

The solution according to the invention lies in a double tube injection-evacuation catheter device comprising
a. One larger [1] and one smaller tube [2], forming a functional unit with the smaller tube [2] positioned within the larger tube [1],
b. both tubes are relocatable and demountable,
c. both tubes with an aperture [3 and 4] at both ends,
d. one aperture [5] being provided in the wall of the outer tube located at a distance of about between 5 mm and 40 mm from the tip [6], or several apertures positioned in a segment of 5-250 mm from the tip, wherein the diameter of the single aperture is between 70% and 120% of the inner diameter of the outer tube [1], or in case of several apertures, for each aperture 30-60% of the inner diameter of the outer tube; in case of several apertures: size, shape and distribution are provided in a way providing uniform deployment of a (foam) sclerosant.
e. wherein the outer diameter of the inner tube is between 0.6 mm and 2.0 mm (F2 to F6), and the inner diameter 0.3-1.6 mm, more preferably 0.4-1.0 mm and even more preferably 0.5-0.8 mm.
f. the outer diameter of the outer tube is between 1.3 mm and 3.3 mm (F4 to F10), and the inner diameter 1.1-3.0 mm, preferably 1.1-3.0 mm and even more preferably 1.1-2.7 mm,
g. a distance between the outer wall of the inner tube and the inner wall of the outer tube is between 0.1 mm to 3.0 mm, preferably 0.1 to 2.5 mm and even more preferably 0.1-2.0 mm.

In specific embodiments, the catheter has one or more of the following dimensions:
Outer tube's outer diameter: 1.3-2.8 mm, preferably 1.5-2.6 mm, more preferably 1.7-2.4 mm.
Outer tube's inner diameter: 1.0-2.4 mm, preferably 1.4-2.0 mm, more preferably 1.2-1.8 mm.
Outer tube's wall diameter/thickness: 0.1-0.3 mm, preferably 0.125-0.25 mm, more preferably 0.15-0.2 mm.
The distance between tip hole and side hole(s) may be greater than 1×, preferably 2-50×, more preferably 20-30× of the outer tube's inner diameter.

Ideally both tubes are visible in ultrasound imaging, or in another embodiment also in fluoroscopy, phlebography, CT or MRI.

In some embodiments the tip zone of the outer tube is modified such that a flow resistance occurs at the tip. A flow resistance may be achieved by narrowing the inner diameter of the outer tube towards the tip. The outer diameter may remain unchanged or decrease as well at the tip zone resulting in a tapered outer tube. If a tapered outer tube is used, the catheter device may be conveniently introduced into the vein with a lesser risk of damaging the vessel. A flow resistance at the tip zone increases the flow through the side hole(s). Most applications of the present invention make a 100% flow of the foam through the side hole(s) desirable. Preferably, the outflow area formed by the outer tube's tapered tip is smaller than the outflow area formed by the side hole(s).

The catheter dimensions and in particular the side holes are of major importance. All formerly manufactured so called aspiration catheters aim at the collection of thrombus in arteries or veins. Some are merely tubes with a relatively thin wall and hence offer a large lumen. Other catheters provide side holes of small dimensions for the purpose of distributing contrast agent (angiography), or lytic agents (thrombolysis). The present invention is particularly designed for use in veins. Veins are vessels with a very thin and soft wall. The vessels are often tortuous. A vein catheter has to follow the vascular bends, therefore it has to be rather flexible. At the same time, the catheter must provide a certain pushability or stiffness, to reach all the target area.

The side holes [5] (FIG. 3) have to be relatively large, for two purposes: Large holes allow simple evacuation, end even more importantly, large holes allow the application of foam sclerosants without destroying the foam bubbles, while small holes do. "Large" may be defined by at least 20 times the average foam bubble diameter.

Catheters with one large single side hole are suitable when dealing with single side branch or single perforator vein problems, as these structures can be evacuated from blood and filled with sclerotic agent in a selective way. Catheters with more side holes will perform better when applied in large, straight vessels. When applying negative pressure on a multi-side hole catheter, in the evacuated regions the vein wall will close the side hole(s) like a valve, focusing the negative pressure on the area being subject to gluing.

To reach the aim of uniform and precise foam sclerosant deployment, the side hole design was adapted to the foam viscosity. For a certain foam for example the side hole size at a position of 10 cm distal to the tip [6] may start with a diameter of 50% relative to the catheters inner lumen, and continue towards the tip with 11 further side holes with diameters reduced stepwise for +2.5% (FIG. 4).

The use of the outer tube alone will provide a very uniform and precise application of foam sclerosant, with a so far unknown quality (FIG. 5a,b). However, without additional gluing, it would not fix the vessel to the aimed size.

The position of the catheter/catheters can only be monitored by vision or palpation in very superficial veins (skin level). Under ultrasonography monitoring even tortuous vessels can be followed. If ultrasound imaging should be limited (obesity, scars, gas echoes), a monitoring of catheters can be performed by fluoroscopy or phlebography. If an imaging method using x-ray contrast media is chosen, these media can be applied via the inner or the outer catheter, depending on the desired amount and the degree of blood replacement.

The outer catheter allows administration of contrast media while functional probes (catheter for gluing, laser- or radiofrequency probes, steam or sclerotherapy catheters) are in place. Large amounts of contrast medium can be picked up by use of the aspiration function of the outer catheter which is in particular an advantage in patients with sensitivities against contrast media. In patients with intolerance or increased risks of contrast media, fluid contrast media usually containing iodine can be replaced by carbon dioxide. Also carbon dioxide may be picked up by aspiration or by opening the outlet via the outer catheter.

In a particular embodiment, the outer tube [1] consists of two relocatable layers or tubes, adding an additional tube [8] of 0.1-0.6 mm wall thickness to the outer tube [1], spaced apart at 0.1-0.5 mm. The task of the additional tube is to cover or uncover the wall apertures of the outer catheter by sliding it back and forth. In one embodiment, it has a proximal grip [10], or handle [11], for easier relocation (FIG. 6e). In another embodiment, there are proximal markings [9], FIG. 6b, on the tubes, or signal device on or within the tube, to indicate the covering status of the outer catheters wall apertures. In a further embodiment, the aperture covering tube has a tapered tip. Its maximal length is defined by the length of the outer catheter minus the length of the side hole area.

The modality using an additional tube [8] to cover or uncover some or all side holes of the outer tube gives the option to use the same catheter for several purposes, like treating straight diseased vessels and single side branch or perforator lesions in the same catheter intervention using one single access. It further more gives the unique option to change from side hole absorption to front hole absorption by covering the side holes.

Preferably, the length of the inner and the outer tube [1, 2] is between 6 cm and 120 cm. The length of the inner tube [2] is always longer than the outer tube [1], with an exceeding length varying from 0.1-140 cm.

The length is defined by the length of the segment with the maximum length that is to be treated. The distance from the groin to the ankle defines the maximum treatment length, but most of the indications have a much shorter segment.

Ideally, the wall thickness of the outer tube is between 0.1-0.6 mm. Preferably, the wall thickness of the outer tube is 0.1 mm-0.3 mm, more preferably 0.125 mm-0.25 mm, most preferably 0.15 mm-0.2 mm. The wall thickness of the inner tube is ideally between 0.1 mm and 0.4 mm.

Figure 7A:
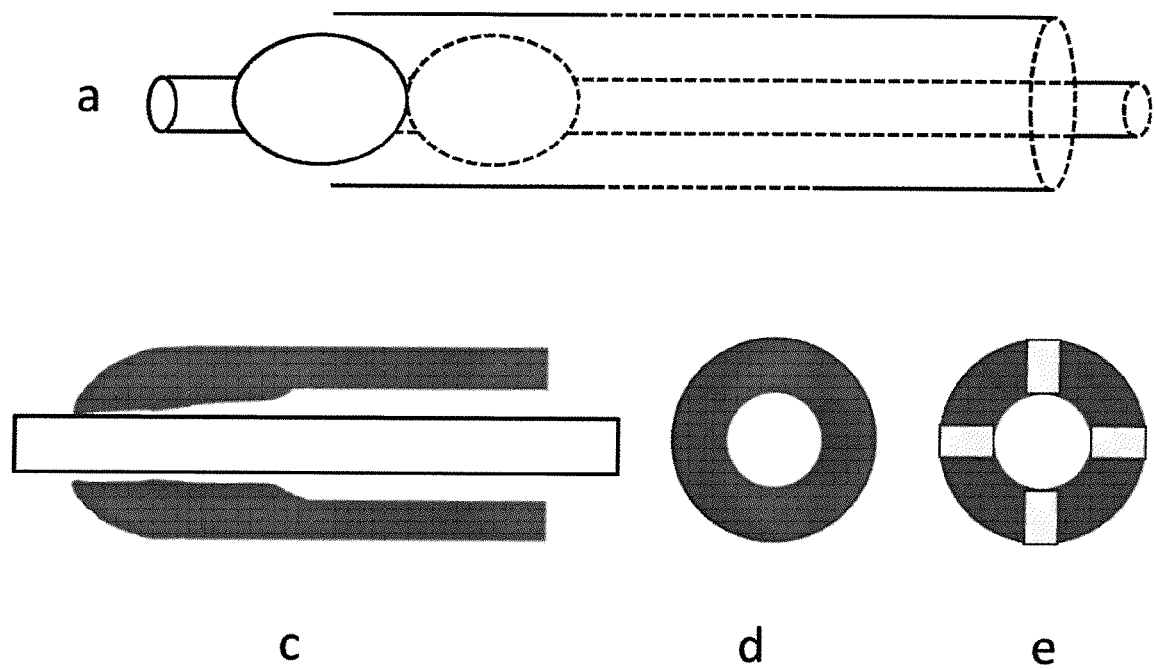

It is preferred, that the outer tube [1] has a terminal tip-zone at which the lumen diameter is reduced in total or in parts to provide guidance for the inner tube (FIG. 7a). Alternatively, the inner tube [2] may have a terminal enlargement with or without increasing the wall thickness, with the purpose of fixation of the inner catheter within the outer catheter, while maintaining the property of easy sliding of the inner tube within the outer tube (FIG. 7a).

Preferably, the outer tube and/or inner tube are equipped at their ends [7], with a male or female Luer-lock connector, or another connector type, and/or are connected with an included or separate Y-shaped or T-shaped piece enabling conduction of the inner tube through the entry of the outer tube as well as flushing or evacuation by way of the outer tube, in one embodiment with a grip zone or a handle for easier sliding movements.

The Luer taper is a standardized system of small-scale fluid fittings used for making leak-free connections between a male-taper fitting and its mating female part on medical and laboratory instruments, including hypodermic syringe tips and needles or stopcocks and needles. Named after the 19th century German medical instrument maker Hermann Wülfing Luer, it originated as a 6% taper fitting for glass bottle stoppers. Key features of Luer Taper connectors are defined in the ISO 594 standards. It is also defined in the DIN and EN standard 1707:1996 and 20594-1:1993.

Preferably, one, several or all tubes have a tapered tip [6] (FIG. 7a). It is most preferred that all tubes have a tapered distal terminal tip for easier introduction into the target vein.

Preferably, the inner and/or outer tube is made of or covered with anti-sticking material like polytetrafluoroethylene (PTFE), also known as Teflon or perfluoroalkoxy (PFA). It is preferred that the inner and outer tube is made of or covered with polytetrafluoroethylene (PTFE) also known as Teflon, or PFA, or FEP, or similar plastic material with properties protecting the material from sticking to arbitrary substances. This has been shown to be of great importance as it ensures that the glue and the possibly remaining blood fractions do not stick to the device. Polytetrafluoroethylene (PTFE) is a synthetic fluoropolymer of tetrafluoroethylene that finds numerous applications. The most known brand name of PTFE is Teflon by DuPont Co. PTFE is a fluorocarbon solid, as it is a high-molecular-weight compound consisting wholly of carbon and fluorine. PTFE is hydrophobic: neither water nor water-containing substances wet PTFE, as fluorocarbons demonstrate mitigated London dispersion forces due to the high electronegativity of fluorine.

PTFE has one of the lowest coefficients of friction against any solid body. PTFE is used as a non-stick coating for pans and other cookware. It is very non-reactive, partly because of the strength of carbon-fluorine bonds, and so it is often used in containers and pipework for reactive and corrosive chemicals. It is also used for catheters. Perfluoroalkoxy or PFA is a type of fluoropolymer with properties similar to polytetrafluoroethylene (PTFE). It differs from the PTFE resins in that it is melt-processable using conventional injection molding and screw extrusion techniques. PFA was invented by DuPont and is sold under the brandname Teflon PFA. Teflon is better known as the trade name for PTFE.

Other brandnames for granules are Neoflon PFA from Daikin or Hyflon PFA from Solvay Solexis. PFA is very similar in composition to the fluoropolymers PTFE and FEP (fluorinated ethylene-propylene). PFA and FEP both share PTFE's useful properties of low coefficient of friction and non-reactivity, but are more easily formable. PFA is softer than PTFE and melts at 305° C.

It is preferred that the inner and/or outer tube comprise means for fixing the position of the two conduits with respect to each other, such as a broadening, hooks or locks.

It is preferred that the inner and/or outer conduits are combined in the following size configurations (outer diameter):

TABLE 1

| Outer tube | F4 | F5 | F6 | F7 | F8 | F9 | F10 |
|---|---|---|---|---|---|---|---|
| Inner tube | F1-2 | F2-3 | F2-4 | F2-5 | F2-6 | F2-7 | F2-8 |

The French scale or French gauge system is commonly used to measure the size (outside diameter) of a catheter. It is most often abbreviated as Fr, but can often abbreviated as FR or F. It may also be abbreviated as CH or Ch (for Charrière, its inventor) in French speaking countries. 1 Fr=0.33 mm, and therefore the diameter of the catheter in millimeters can be determined by dividing the French size by 3:

$$D \text{ (mm)}=Fr/3 \text{ or } Fr=D \text{ (mm)} \times 3$$

For example, if the French size is 9, the diameter is 3 mm.

An increasing French size corresponds to a larger diameter catheter. This is contrary to needle-gauge size, where an increasing gauge corresponds to a smaller diameter catheter. The French gauge was devised by Joseph-Frédéric-Benoît Charrière, a 19th-century Parisian maker of surgical instruments, who defined the "diameter times 3" relationship; See table 2.

TABLE 2

| French (F) | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |

It is preferred if one of the tubes comprises a guide wire (0.14-0.38 inch).

Ideally, the tip zone of the inner and/or outer tube is shaped or shapeable for a distance of 1-4 cm to form a curve, covering an angle from 5 to 90 degrees, serving as tool to probe venous curves, junctions, a side branches or perforator veins (FIG. 2).

The invention relates to a double-tube injection and aspiration catheter device, wherein the inner tube is replaced, exchanged, replaceable or exchangeable by a metal or metal-like hollow needle with a double- or triple-cut tip.

Figure 7B:
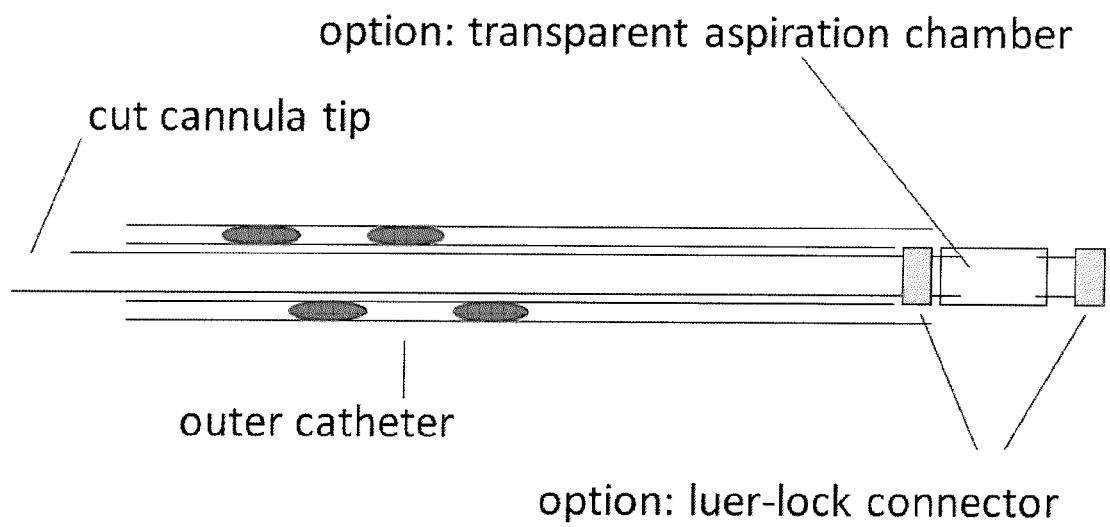
Figure 8A:
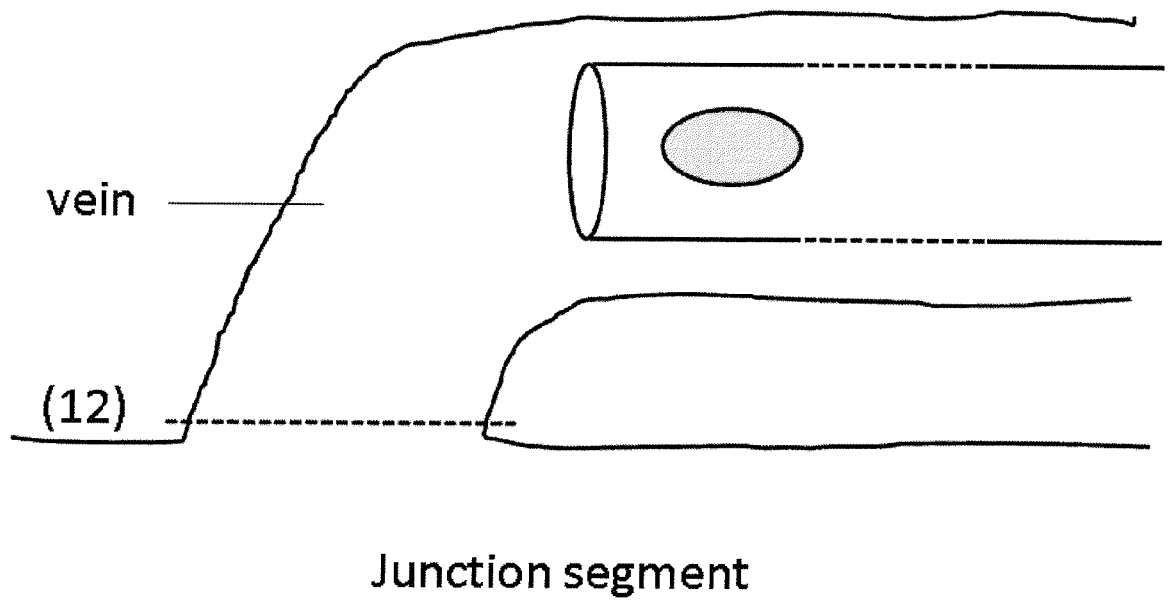
Figure 8B:
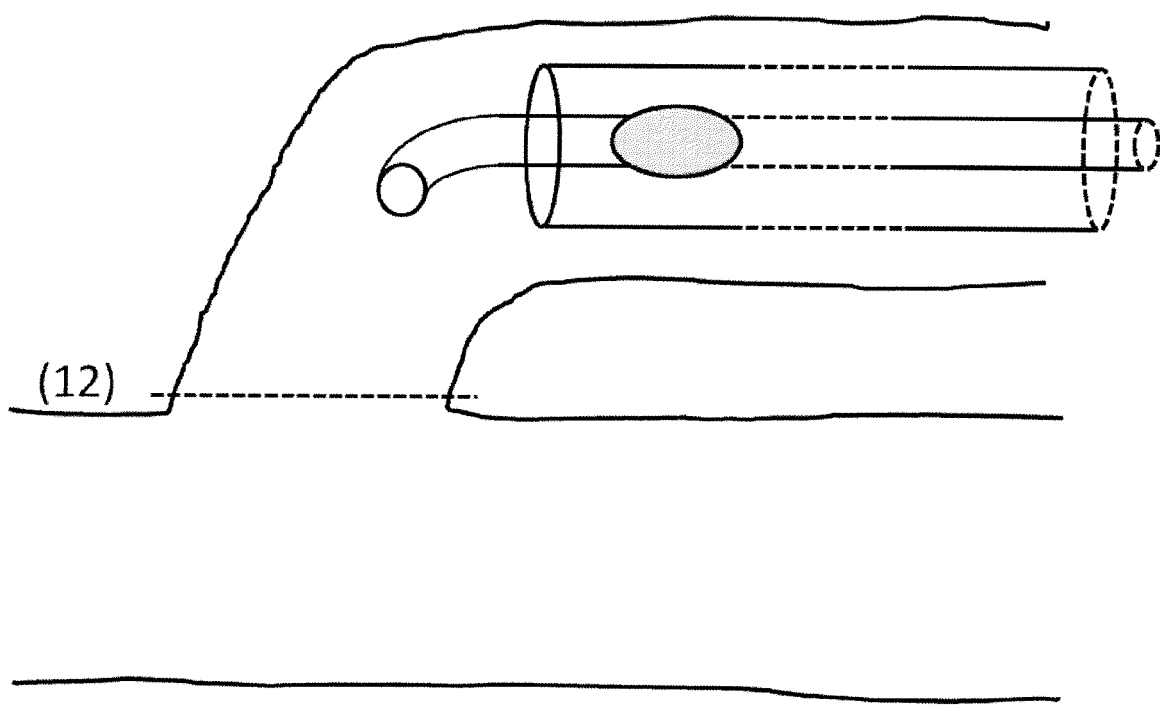
Figure 8C:
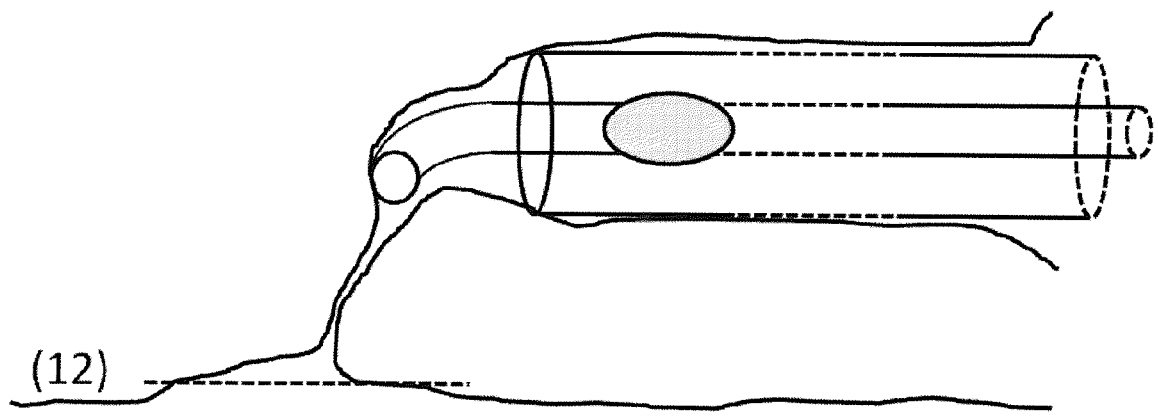
Figure 8D:
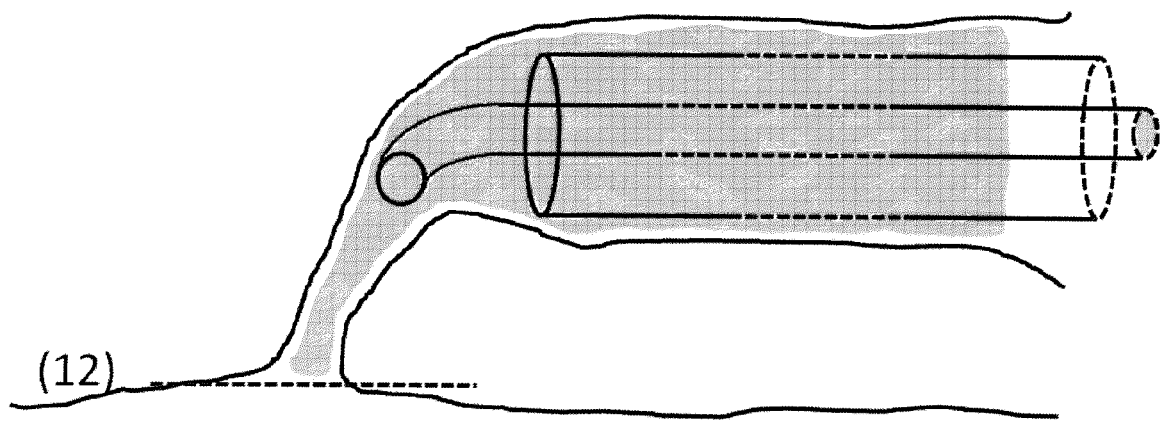
Figure 8E:
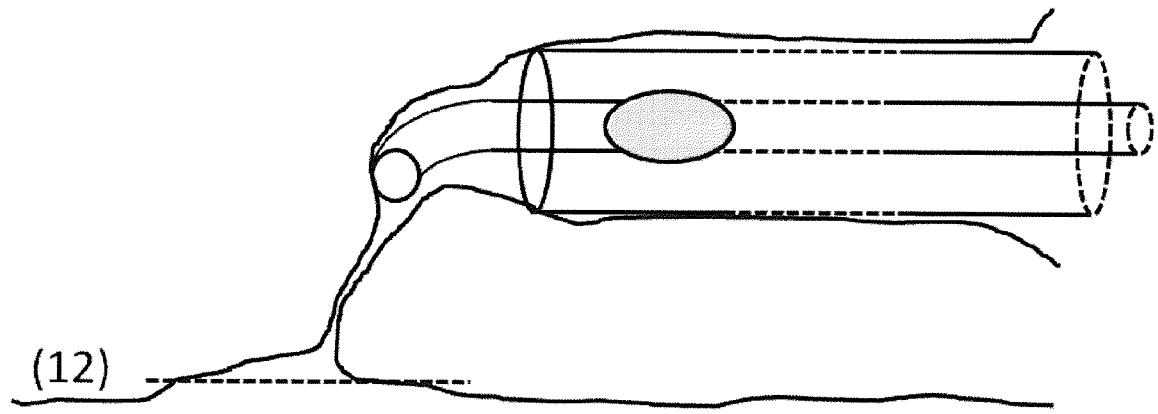
Figure 8F:
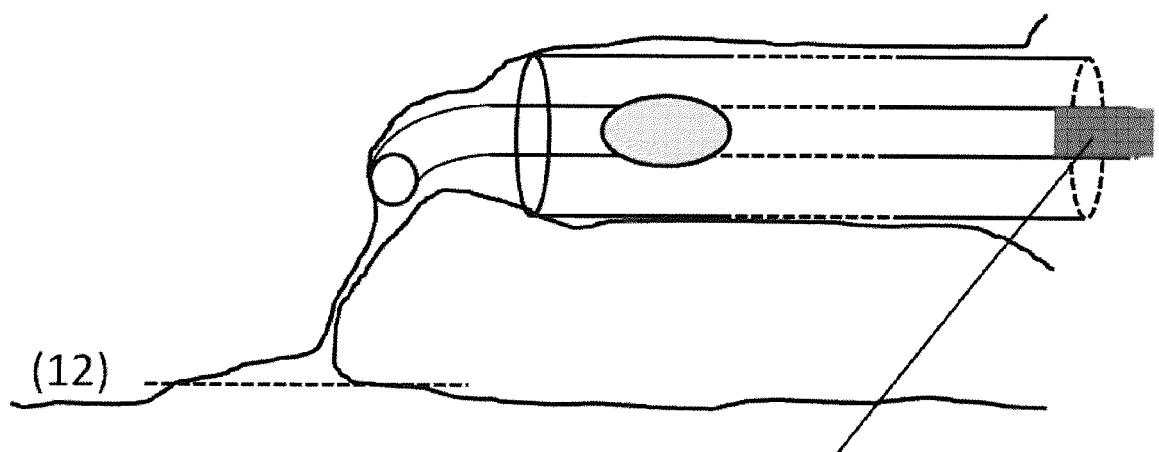
Figure 8G:
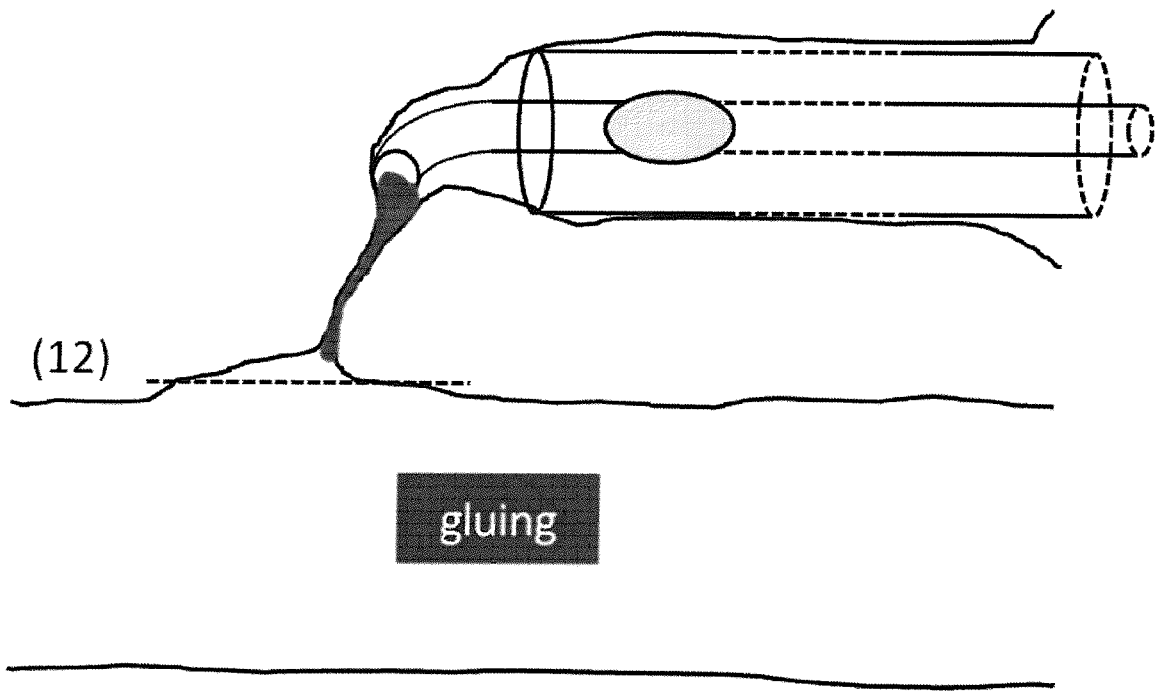
Figure 8H:
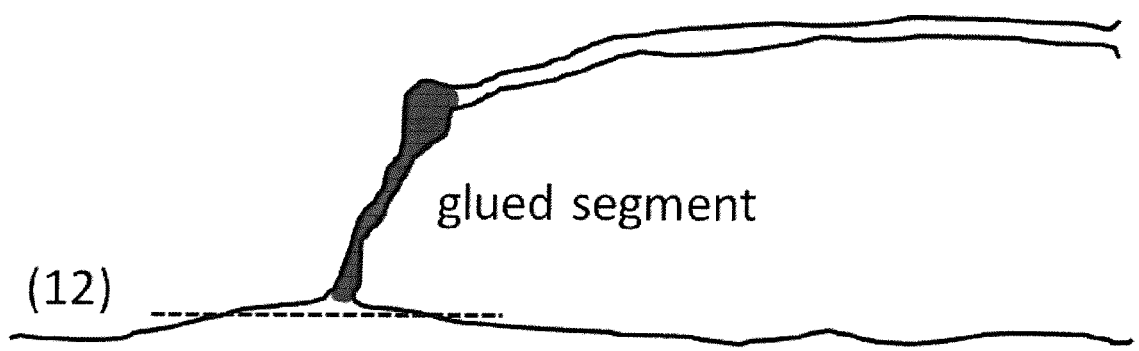
Figure 9A:
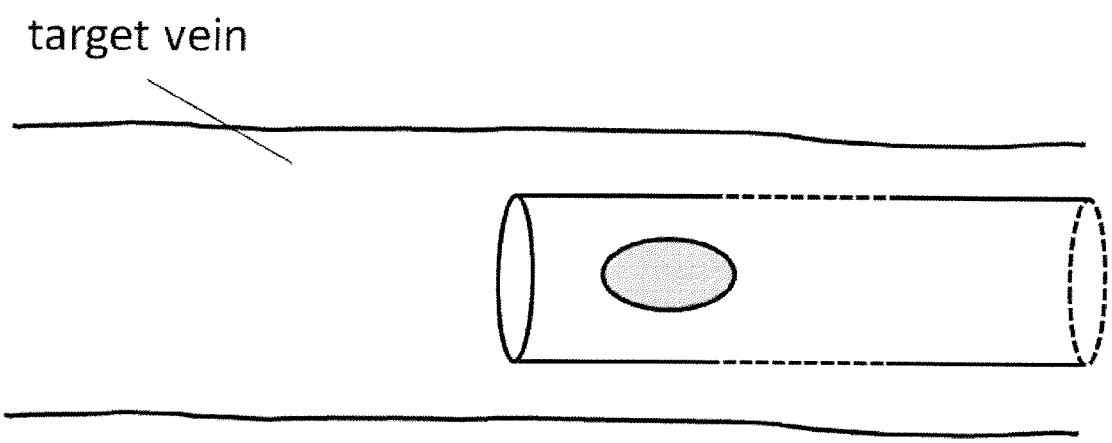
Figure 9B:
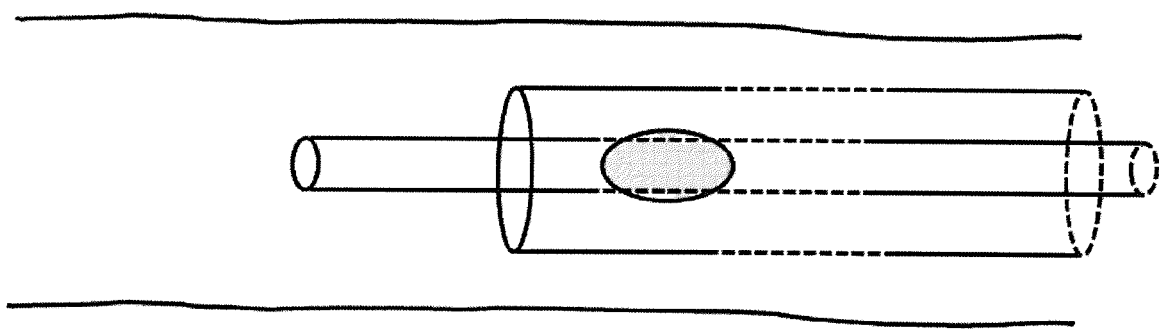
Figure 9C:
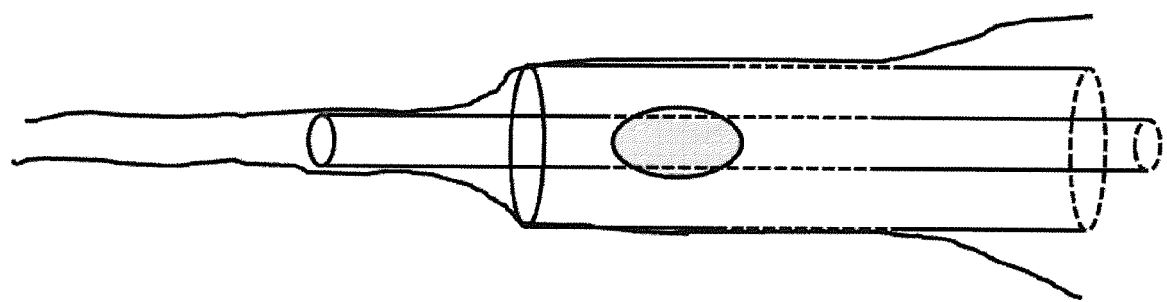
Figure 9D:
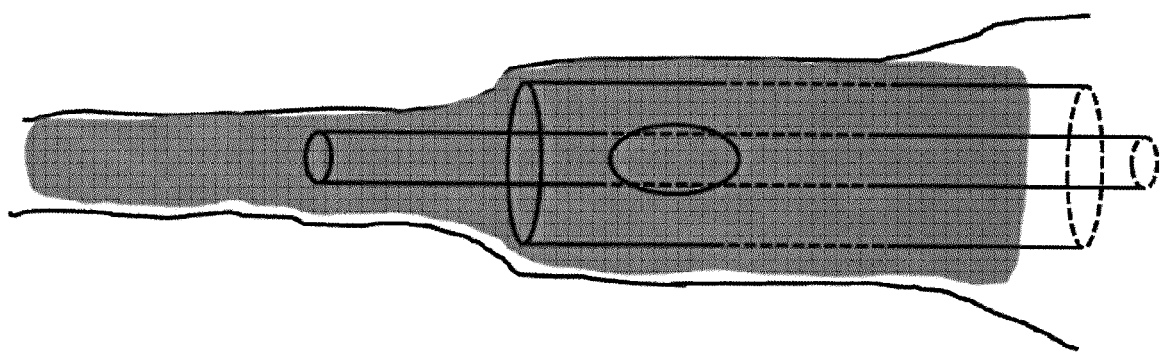
Figure 9E:
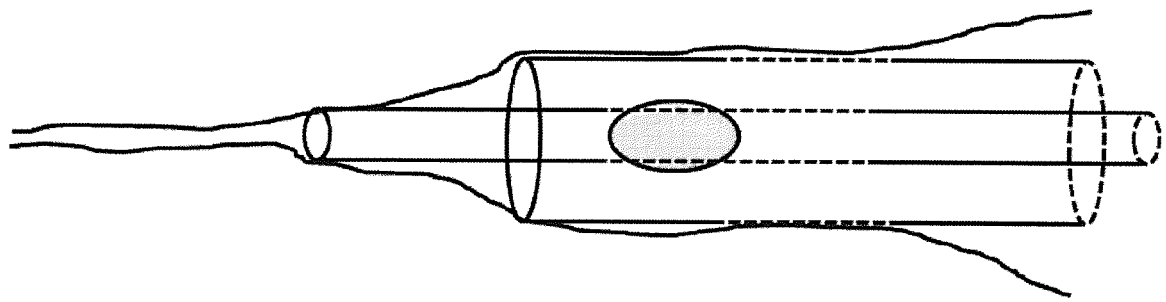
Figure 9F:
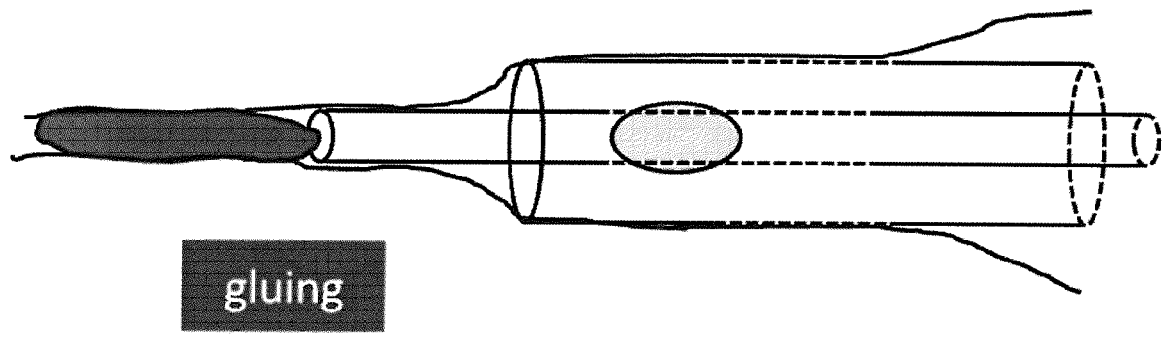
Figure 9G:

If choosing a short and small catheter configuration, e.g. outer diameter (OD) F4, length 6-20 cm, a direct introduction to the target vessel can be achieved by adding a hollow needle, fitting in the outer catheter, preferably with double- or triple cut tip (FIG. 7b).

The double-tube injection may comprise a transparent aspiration chamber (FIG. 7b).

The invention further relates to a composition comprising a) a pharmaceutically acceptable tissue glue, wherein the glue can polymerize on contact with $H_2O$, blood or constituent parts of blood, and b) a medical gas, for use in treating varicose veins.

It may further comprise a sclerosant drug. Preferably the composition additionally comprises a sclerosant drug. Foam sclerotherapy is a technique that involves injecting "foamed sclerosant drugs" within a blood vessel using a syringe—here the inventive catheter. The sclerosant drugs (e.g. sodium tetradecyl sulfate or polidocanol) are mixed with air or a physiological gas (e.g. carbon dioxide, oxygen) in a pair of syringes, by using mechanical or electro-mechanical pumps, or gas pressure. Foaming increases the surface area of the drug. The foam sclerosant drug is more efficacious than the liquid for it does less mix with the blood in the vessel and rather displaces it, thus avoiding dilution of the drug and causing maximal sclerosant action.

It is very astonishing that the inventors have found that the sclerosant drug when used with the presented aspiration-injection catheter, leads to much better results than foam sclerotherapy by needle or plain tube catheter injection. A vein spasm is the effect of the drug. When glue that is applied at a time the drug-induced spasm persists, it will fix the vein in a status with largely reduced diameter.

It could also be observed that due to the sclerosant agent and the triggered spasm the vein has micro wrinkles which are an ideal surface for the glue. These effects are supported by the negative aspiration pressure, guiding the glue to all intraluminal areas.

Ideally the glue is selected from the list of cyanoacrylate and fibrin glue. Cyanoacrylate is preferred. Cyanoacrylate is the generic name for cyanoacrylate based fast-acting adhesives such as methyl 2-cyanoacrylate, ethyl-2-cyanoacrylate (commonly sold under trade names like Super Glue and Krazy Glue), and n-butyl cyanoacrylate (used in veterinary and skin glues). The related compound 2-octyl cyanoacrylate is a medical grade glue; it was developed to be non-toxic and less irritating to skin tissue.

Ideally, the glue is in the form of a gel, foam or emulsion.

The medical gas is selected from the list of carbon dioxide, oxygen, air, or mixtures hereof.

Preferably, the glue and gas are loaded in the device and/or applied in subsequent boli.

The inventors have found that smallest amounts of fluid or blood lead to a fast polymeric glue reaction of cyanocrylates. Therefore the injection of glue in blood containing vessels does never allow an appropriate distribution of the glue. The glue will polymerise more or less in clots, not reaching all parts of the vein wall. In the invention, the outer tube serves in a first step to aspirate blood from the target vein segment until the vein is empty and collapsed. The side hole or several side holes enforce the aspiration capacity, as the front hole may be occluded by thrombus, by parts vein wall when pushed through curves, or within ectasias or aneurysms. The intraluminal position of the side holes may be changed by twisting the catheter. Even blood inflow from venous side branches or perforator veins (connecting veins to the deep venous system) may be aspirated by use of the side holes. Aspiration serves as a preparation for the following glue application. It furthermore serves to deploy sclerosant, and to remove sclerosant foam before gluing.

It has been found that cyanoacrylate or a fibrin glue may be brought into veins more effectively if a small amount of medical gas is used at the same time. The gas may be used a) to prepare a foam or gel glue, or b) a gas-glue-gas combination while loading the components subsequently in the inner tube. The term "glue" refers to a fluid, a gel or a foam. Gas serves to prepare the glue injection site, as it cleanses the gluing site. The inner catheter is used to introduce both glue and gas. Gas is introduced first, then the glue is introduced. Upon inserting the glue, gas is introduced again. The second bolus of gas is meant to clean the tool. Gas will not accumulate in the target vessel as it is evacuated immediately by the negative pressure mediated by the outer tube.

Using portions of gas proceeding and following the glue, small but effective amounts of glue can be applied without leaving useless remnants within the catheter. The proceeding portion of gas will displace remnants of blood or sclerosant agent and prepare the segment for gluing. By use of the aspiration function of the outer catheter, even gas remnants can be eliminated so the glue meets a totally collapsed vein. Without the outlet via the outer catheter, it is not possible to inject portions of glue and gas, as in case of a resistance gas would pass the glue within the catheter, and glue would stay inside without moving. The negative pressure maintained by the aspiration catheter first allows the gas to pass, and then it will press the vein walls together while the glue fixes them in this position.

In an alternative no gas is used. Here, the catheter must have a special material as outlined below. In this case, glue (fluid, gel, or foam) can be applied under negative pressure in a continuous mode during withdrawal of the system.

Preferably, the glue and gas are loaded in a 1:1 to 1:4 ratio prior to application. Preferably, $CO_2$ or $CO_2/O_2$ (70/30) is used. The preferred amount of glue per injection is 0.1-0.5 ml. Using this amount, a vein segment of 1-10 cm can be treated. It could be shown that continuous gluing does not offer advantages in comparison to the proposed modality of sclerotherapy and point wise gluing. In opposite, continuous gluing will rather leave an unwanted stiffness of the treated vein.

The invention relates to a kit comprising a pharmaceutically acceptable glue, wherein the glue can polymerize on contact with $H_2O$, blood, or constituent parts of blood, and a sclerosant drug.

The kit preferably further comprises a catheter.

In the kit according to the invention the glue is selected from the list of cyanoacrylate and fibrin glue, and/or the medical gas is selected from the list of carbon dioxide, oxygen, air, or mixtures thereof.

The kit according to the invention may have a guide-wire, and/or an introduction aid for puncture and guide wire insertion.

The invention also relates to a kit wherein the catheter system includes chambers, cartridges or syringes to contain or deploy glue, sclerosant, foam, gas or blood.

It also relates to a kit wherein the catheter system includes mechanic, pneumatic, hydraulic or electric/electronic means to support or perform injection and/or aspiration.

EXAMPLES

Example 1

Treatment of an insufficient greater saphenous vein, diameter 10-14 mm in the standing patient, length of insufficient segment: 45 cm. Selected tool: double-tube injection-aspiration catheter system, working length 75 cm, with an outer diameter of 7F with a 5 cm side hole area and 12 side holes, and an inner tube size F4. Venous access by using a hollow needle or (preferred) a venula of a size of about 80% of the chosen outer catheter's diameter, in local anaesthesia. This diameter will prepare the vein entry for the introduction of the slightly bigger catheter system. All steps are performed under ultrasound view. Target vein access with a hydrophilic guide wire of known glidewire type, size 0.35", then introduction of the outer catheter unto tip reaches intended point of proximal closure at the femorosaphenous junction. Withdrawal for approx. one centimeter. Mounting of inner tube and positioning at same region. Aspiration of blood via outer tube until junction segment collapses. Application of 1 ml polidocanol foam, mixed 1+4 with air, via outer tube. Withdrawal of outer tube for another 2 centimetres, leaving inner tube in previous place. Absorption of foam after 60 s. The vein is collapsed by negative pressure and spasm. Negative pressure is maintained. Loading of inner tube with sequences of 0.8 ml CO2 and 0.2 ml cyanoacrylate (Ethyl 2-Cyanoacrylate/Polymethylmethacrylate).

Application of one sequence under ultrasound view while retracting inner catheter for one centimetre. Maintaining of negative pressure for 60 s. Withdrawal of system for 5 cm, repetition of procedure. Procedure is continued same way until whole target segment is closed. Venous access site is closed with a final portion of glue from the inner tube while retracting through skin. Proof by ultrasound imaging in the standing patient: Diameter of treated vein is 2-3 mm. No compression bandage or stocking required. Immediate ambulation.

Example 2

Varicose vein at the lower limb, diameter in the standing patient 8-12 mm, length 31 cm, very tortuous, filling from a perforator vein defect in the region BOYD. Selected Tool: Double-lumen aspiration-injection catheter system with outer diameter F5, length 20 cm, with a double- or triple-cut tip hollow needle of 1.0 mm outer diameter, and an inner tube of 0.8 mm outer diameter. The diseased segment is treated in two steps, beginning with the proximal part. Direct puncture of target vein 15 cm below the source of backward blood flow, using outer tube plus hollow needle. Navigation through tortuosities under ultrasound view unto the entry of perforator vein. Withdrawal of hollow needle. Introduction of inner tube into the perforator vein. Aspiration of blood until perforator vein collapses. Deployment of 0.5 ml sclerofoam, residence time 60 s. Loading of inner tube with sequences of 0.8 ml CO2 and 0.2 ml cyanoacrylate (Ethyl 2-Cyanoacrylate/Polymethylmethacrylate). Aspiration of foam remnants and blood. Application of 0.2 ml glue, negative pressure maintained via outer catheter for 60 s. Withdrawal of system for 3 cm. Repetition of procedure. 2× withdrawal for 5 cm, same procedure. Venous access closed with a small drop of glue from the inner catheter. Then the system is remounted to outer tube plus hollow needle, second access 20 cm below, probing of second half of diseased vein, and closure in 3 steps like previously described. Venous access closed with a small drop of glue from the inner catheter. The varicosity is no more visible while the patient is in horizontal position. In the standing patient, the result remains the same. No compression bandage or stocking required. Immediate ambulation.

FIGURE CAPTIONS

FIG. 1:
a) The basic parts of the system: Outer tube [1], inner tube [2], position when mounted.
b) endovenous approach to target vein segment FIG. 2:
Inner tube [2], examples of embodiments: a) straight tip, b) straight tip with side holes, c) flat-angled tip with side hole, d) sharp angled tip.

FIG. 3:
Outer catheter with side holes [5] in the tip section [6].

FIG. 4:
Catheter with calculated side hole dimensions and position provides uniform and distinct foam sclerosant propagation along target vein with outstanding precision, based on uniform pressure distribution.

Figure 5B:
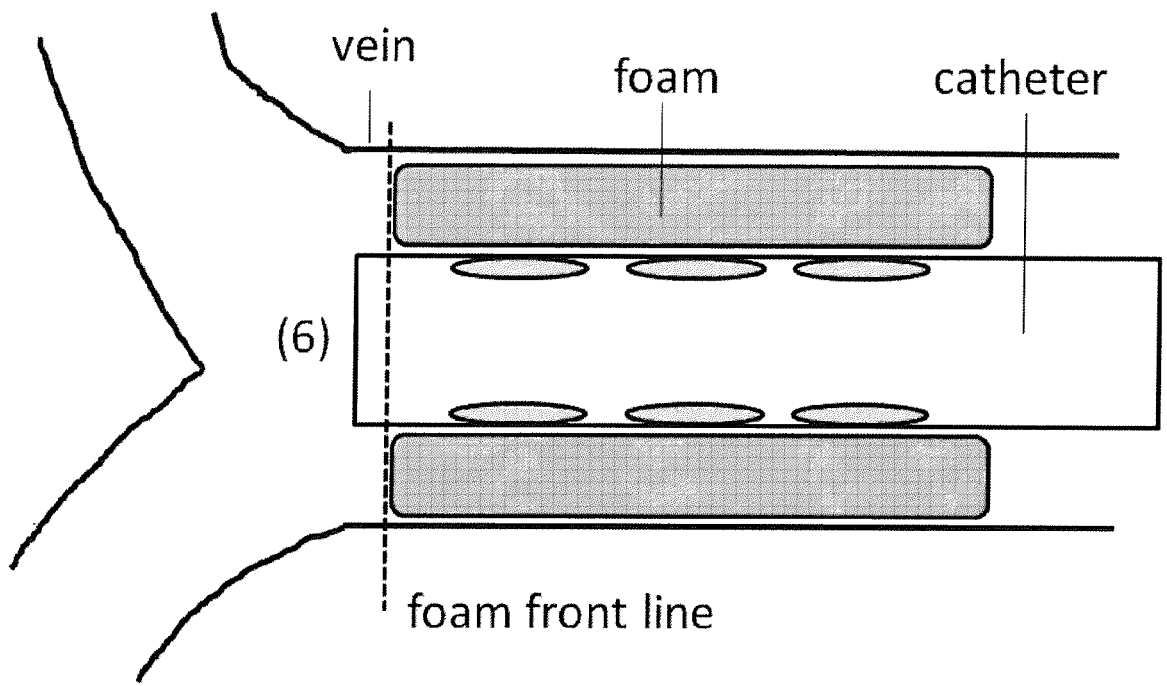

FIG. 5:
a) The space taken by the catheter should equal the space taken by the foam sclerosant.
D=diameter of vein in the patient in horizontal position, d=diameter of the catheter.
The condition for optimal sclerofoam treatment is fulfilled when $(d/2)^2 \times \pi = (D/2)^2 \times \pi - (d/2)^2 \times \pi$ b) Schematic illustration: a) cross section; b) longitudinal cut showing uniform and precise foam distribution around catheter.

FIG. 6:
Additional tube [8], covering or uncovering the side holes of the outer tube, a) cross-sectional view; b) side holes of outer catheter covered by additional tube [8], c) single side hole uncovered, d) multiple side holes uncovered. e) The additional tube [8] may have a grip zone [10], or handle [11], for easier sliding action, and markings to indicate the additional catheter's position [9].

FIG. 7:
Catheter options: a) elevations of inner tube at distal tip to stabilize position within outer catheter; b) narrowing of outer catheter to fix inner catheter, both options either covering the whole circumference (e) or parts of it (e).

FIG. 8:
Typical application at a junction segment, a) positioning of outer tube relative to position of treatment border [12], b) position of inner tube, c) evacuation of blood and target segment collapse, d) application of sclerofoam, e) vein spasm, evacuation of foam, f) system loaded with glue or glue-gas compositions, g) application of glue, h) withdrawal of system to next position, treated vein segment permanently closed.

FIG. 9:
Typical application at a non-junction segment, a) positioning of outer tube, and b) inner tube, c) evacuation of blood until vein segment collapses, d) application of sclerofoam, e) vein spasm, evacuation of foam, f) application of glue, g) system withdrawal to next position, treated vein segment permanently closed.

The invention claimed is:

1. A kit comprising:
a pharmaceutically acceptable tissue glue that can polymerize on contact with $H_2O$, blood, or constituent parts of blood,
a medical gas, for use in treating varicose veins, and
a sclerosant drug,
wherein said medical gas is configured to be combined with said tissue glue to prepare a foam or gel glue for injection within a vein,
the kit further comprising a catheter having an outer tube and an inner tube, the outer tube being fluidly isolated from the inner tube and having at least one side hole provided therein,
wherein the outer tube of the catheter is designed to evacuate blood from a target vein, and to administer and withdraw the sclerosant drug through one or more holes of the at least one side hole, and the inner tube of the catheter is designed to administer a composition comprising the pharmaceutically acceptable tissue glue and the medical gas, wherein the inner tube of the catheter is configured to administer said tissue glue and said medical gas in a 1:1 to 1:4 ratio, and wherein the inner tube of the catheter is configured to administer said tissue glue in an amount of 0.1 mL to 0.5 mL per injection.

2. The kit according to claim 1, wherein the outer tube contains the sclerosant drug, and wherein the inner tube contains the foam or gel glue.

3. The kit according to claim 2, wherein the outer tube has opposing ends and a wall extending between the opposing ends, and wherein at least one aperture is defined within the wall of the outer tube.

4. A method of treating a subject using a kit having a composition and a double tube injection and aspiration catheter, the method comprising:
intravenously applying, at one or more sites of treatment, the composition by the double tube injection and aspiration catheter, the catheter having an outer tube and an inner tube, the outer tube having at least one side hole provided therein, the composition comprising:
a) a pharmaceutically acceptable tissue glue that can polymerize on contact with $H_2O$, blood or constituent parts of blood,
b) a medical gas, for use in treating varicose veins, and
c) a sclerosant drug; and
performing the following steps at each of the one or more sites of treatment:
aspirating blood of the subject through one or more holes of the at least one side hole provided in the outer tube to collapse a vein;
administering the sclerosant drug as a first foam through one or more holes of the at least one side hole provided in the outer tube;
aspirating the sclerosant drug through one or more holes of the at least one side hole provided in the outer tube; and
applying the tissue glue and medical gas via the inner tube as a second foam or gel while maintaining negative pressure via the outer tube,
wherein said medical gas is combined with said tissue glue to prepare the second foam or gel for injection within the vein,
wherein said tissue glue and said medical gas are applied in a 1:1 to 1:4 ratio, and
wherein said tissue glue is provided in an amount of 0.1 mL to 0.5 mL per injection.

5. The method according to claim 4, wherein the tissue glue is selected from the list of cyanoacrylate and fibrin glue.

6. The method according to claim 4, wherein the medical gas is selected from the list of carbon dioxide, oxygen, air, or mixtures thereof.

7. The method according to claim 4, wherein said tissue glue and said medical gas are loaded in the inner tube of the double tube injection and aspiration catheter.

8. The method according to claim 4, wherein said tissue glue and said medical gas are loaded in the inner tube of the double tube injection and aspiration catheter.

9. A method of treating a subject using a kit having a composition and a double tube injection and aspiration catheter, the method comprising:
intravenously applying, at one or more sites of treatment, the composition by the double tube injection and aspiration catheter, the catheter having an outer tube and an inner tube, the outer tube having at least one side hole provided therein, the composition comprising:
a) a pharmaceutically acceptable tissue glue that can polymerize on contact with $H_2O$, blood or constituent parts of blood,
b) a medical gas, for use in treating varicose veins, and
c) a sclerosant drug; and
performing the following steps at each of the one or more sites of treatment:
aspirating blood of the subject through one or more holes of the at least one side hole of the outer tube to collapse a vein;
administering the sclerosant drug as a first foam through one or more holes of the at least one side hole of the outer tube;
aspirating the sclerosant drug through one or more holes of the at least one side hole of the outer tube; and
sequentially applying the medical gas and the tissue glue via the inner tube while maintaining negative pressure via the outer tube,
wherein at least a first portion of the medical gas is applied in a first bolus and the tissue glue is subsequently applied in a second bolus, and
wherein said tissue glue and said medical gas are applied in a 1:1 to 1:4 ratio, and
wherein said tissue glue is provided in an amount of 0.1 mL to 0.5 mL per injection.

10. The method according to claim 9, wherein a second portion of the medical gas is applied in a third bolus following application of the second bolus.

11. The method according to claim 9, wherein the tissue glue is selected from the list of cyanoacrylate and fibrin glue.

12. The method according to claim 9, wherein the medical gas is selected from the list of carbon dioxide, oxygen, air, or mixtures thereof.

* * * * *